US008071783B2

(12) United States Patent
Zhang et al.

(10) Patent No.: US 8,071,783 B2
(45) Date of Patent: Dec. 6, 2011

(54) N-HETEROCYCLIC CARBENE CATALYZED SYNTHESIS OF N-PHENYLISOXAZOLIDIN-5-ONE DERIVATIVE AND SYNTHESIS OF β-AMINO ACID ESTER DERIVATIVE

(75) Inventors: Yugen Zhang, Singapore (SG); Jackie Y. Ying, Singapore (SG); Jayasree Seayad, Singapore (SG); Pranab K. Patra, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 265 days.

(21) Appl. No.: 12/531,678

(22) PCT Filed: Mar. 14, 2008

(86) PCT No.: PCT/SG2008/000079
§ 371 (c)(1),
(2), (4) Date: Sep. 16, 2009

(87) PCT Pub. No.: WO2008/115149
PCT Pub. Date: Sep. 25, 2008

(65) Prior Publication Data
US 2010/0099886 A1    Apr. 22, 2010

Related U.S. Application Data

(60) Provisional application No. 60/907,016, filed on Mar. 16, 2007.

(51) Int. Cl.
*C07D 261/04* (2006.01)
*C07C 229/00* (2006.01)
(52) U.S. Cl. .......................... 548/243; 560/38
(58) Field of Classification Search .......... None
See application file for complete search history.

(56) References Cited

OTHER PUBLICATIONS

Abdel-Magid, A. F., et al., *Curr. Med. Chem.* 1999, p. 955-969, vol. No. 6.
Beller, M. et al., *Agnew. Chem., Int. Ed.*, 2004, p. 3368-3398, vol. 43.
Bode, J. W.; Sohn, S. S., *J. Am. Chem. Soc.* 2007, p. 13798-13799, vol. No. 129.
Bøgevig, A. et al., *Angew. Chem., Int. Ed.* 2002, p. 1790-1793, vol. No. 41.
Breslow, R., *J. Am. Chem. Soc.* 1958, p. 3719-3726, vol. No. 80.
Burstein, C.; Glorius, F., *Angew. Chem., Int. Ed.* 2004, p. 6205-6208, vol. No. 43.
Burstein, C., et al., *Synthesis* 2006, p. 2418-2439.
Chan, A.; Scheidt, K.A., *J. Am. Chem. Soc.* 2007, p. 5334-5335, vol. No. 129.
Chen, Y. K., et al., *J. Am. Chem. Soc.* 2006, p. 9328-9329, vol. No. 128.
Chiang, P. -C., et al., *J. Am. Chem. Soc.* 2007, p. 3520-3521, vol. No. 129.
Cole, D. C., *Tetrahedron* 1994, p. 9517-9582, vol. No. 50.
Corbett, M. D., et al., *J. Chem. Soc. Perkin Trans. I* 1982, p. 345-350.
Corbett, M. D., et al., *J. Chem. Soc., Perkin Trans. I* 1983, p. 765-769.
Duong, H. A., et al., *Org. Lett.* 2004, p. 4679-4681, vol. No. 6.
Enders, D.; Kallfass, U., *Angew. Chem., Int. Ed.* 2002, p. 1743-1745, vol. No. 41.
Enders, D.; Balensiefer, T., *Acc. Chem. Res.* 2004, p. 534-541, vol. No. 37.
Enders, D., et al., *Chem. Rev.* 2007, p. 5606-5655, vol. No. 107.
Glorius, F., et al., *Chem. Commun.* 2002, p. 2704-2705.
Guerin, D. J.; Miller, S. J., *J Am. Chem. Soc.* 2002, p. 2134-2136, vol. No. 124.
Hata, S., et al., *Org. Lett.* 2004, p. 1721-1723, vol. No. 6.
He, M., et al., *J. Am. Chem. Soc.* 2006, p. 15088-15089, vol. No. 128.
He, M., et al., *J Am. Chem. Soc.* 2006, p. 8418-8420, vol. No. 128.
Hoffmann, S., et al., *J. Am. Chem. Soc.* 2006, p. 13074-13075, vol. No. 128.
Hultzsch, K. C., *Adv. Synth. Catal.*, 2005, p. 347 & 367-391, vol. No. 347.
Ibrahem, I., et al., *Angew. Chem., Int. Ed.* 2004, p. 6528-6531, vol. No. 43.
Ibrahem, I., et al., *Chem. Commun.* 2007, p. 849-851.
Kano, T., et al., *J. Am. Chem. Soc.* 2006, p. 6046-6047, vol. No. 128.
Kerr, M. S., et al., *J Am. Chem. Soc.* 2002, p. 10298-10299, vol. No. 124.
Kerr, M. S.; Rovis, T., *J. Am. Chem. Soc.* 2004, p. 8876, vol. No. 126.
Kerr, M. S., et al., *J. Org. Chem.* 2004, p. 5725-5728, vol. No. 70.
Kerr, M. S.; Rovis, T., *Synlett* 2003, p. 1934-1936.
List, B., *J. Am. Chem. Soc.* 2002, p. 5656-5657, vol. No. 124.
Liu, M.; Sibi, M. P., *Tetrahedron* 2002, p. 7991-8035, vol. No. 58.
Luisi, R., et al., *J. Org. Chem.* 2003, p. 9861-9864, vol. No. 68.
Ma, J. -A., *Angew. Chem., Int. Ed.* 2003, p. 4290-4299, vol. No. 42.
Margriotis, P. A., *Angew. Chem., Int. Ed.* 2001, p. 4377-4379, vol. No. 40.
Marigo, M.; Jørgensen, K. A.,*Chem. Commun.* 2006, p. 2001-2011.
Marion, N., et al., *Angew. Chem., Int. Ed.* 2007, p. 2988-3000, vol. No. 46.
Mitsuru, S., et al., *Synthesis* 2003, p. 1441-1445, vol. No. 9.
Momiyama, N., et al., *J. Am. Chem. Soc.* 2007, p. 1190-1195, vol. No. 129.
Myers, J. K.; Jacobsen, E. N., *J. Am. Chem. Soc.* 1999, p. 8959-8960, vol. No. 121.
Nair, V., et al., *J. Am. Chem. Soc.* 2006, p. 8736-8737, vol. No. 128.
Phillips, E. M., et al., *Angew. Chem., Int. Ed.* 2007, p. 3107-3110, vol. No. 46.
Porter, J. R., et al., *J. Am. Chem. Soc.* 2001, p. 10409-10410, vol. No. 123.

(Continued)

*Primary Examiner* — Kamal Saeed
(74) *Attorney, Agent, or Firm* — Klarquist Sparkman, LLP

(57) ABSTRACT

A process for preparing a N-phenylisoxazolidin-5-one derivative is provided. The process for preparing the N-phenylisoxazolidin-5-one derivative comprises reacting an α,β-unsaturated aldehyde with nitrosobenzene in the presence of a N-heterocyclic carbene (NHC) catalyst. A process for preparing an N-alkoxyphenyl protected β-amino acid ester derivative is further provided. The process for preparing the N-alkoxyphenyl protected β-amino acid ester derivative comprises reacting an α,β-unsaturated aldehyde with nitrosobenzene in the presence of a N-heterocyclic carbene (NHC) catalyst to form a N-phenylisoxazolidin-5-one derivative, and then treating the N-phenylisoxazolidin-5-one derivative with an alcohol in the presence of an acid catalyst. A process for preparing an N-alkoxyphenyl protected β-amino acid ester derivative, comprising treating a N-phenylisoxazolidin-5-one derivative with an alcohol in the presence of an acid catalyst, is also provided.

19 Claims, No Drawings

OTHER PUBLICATIONS

Seayad, J., et al., *Organic Letters* 2008, p. 953-956, vol. No. 10.
Seebach, D., *Agnew. Chem., Int. Ed.* 1979, p. 239-258, vol. No. 18.
Shine)°, M., et al., *Org. Lett.* 2002, p. 3119-3121, vol. No. 4.
Sohn, S. S., et al., *J. Am. Chem. Soc.* 2004, p. 14370-14371, vol. No. 126.
Verkade, J. M. M., et al., *Tetrahedron Lett.* 2006, p. 8109-8113, vol. No. 47.
Von Franz, N., et al., *Angew. Chem., Int. Ed.* 1998, p. 3292-3295, vol. No. 37.
Vora, H. U.; Rovis, T., *J. Am. Chem. Soc.* 2007, p. 13796-13797, vol. No. 129.
Wadamoto, M., et al., *J. Am. Chem. Soc.* 2007, p. 10098-10099, vol. No. 129.
Xu, L.-W.; Xia, C. G., *Eur. J. Org. Chem.* 2005, p. 633-639.
Yamamoto, H.; Momiyama, N., *J. Am. Chem. Soc.* 2005, p. 1080-1081, vol. No. 127.
Yamamoto, H.; Momiyama, N., *Chem. Commun.* 2005, p. 3514-3525.
Zeitler, K., *Angew. Chem., Int. Ed.* 2005, p. 7506-7510, vol. No. 44.

N-HETEROCYCLIC CARBENE CATALYZED SYNTHESIS OF N-PHENYLISOXAZOLIDIN-5-ONE DERIVATIVE AND SYNTHESIS OF β-AMINO ACID ESTER DERIVATIVE

CROSS REFERENCE TO RELATED APPLICATION

This claims the benefit of U.S. Provisional Application No. 60/907,016, filed Mar. 16, 2007, the contents of which are incorporated herein by reference.

This invention relates to a process for preparing a N-phenylisoxazolidin-5-one derivative comprising reacting an α,β-unsaturated aldehyde with nitrosobenzene in the presence of a N-heterocyclic carbene (NHC) catalyst. The invention also relates to a process for preparing an N-alkoxyphenyl protected β-amino acid ester derivative comprising reacting an α,β-unsaturated aldehyde with nitrosobenzene in the presence of a N-heterocyclic carbene catalyst to form a N-phenylisoxazolidin-5-one derivative, and then treating the N-phenylisoxazolidin-5-one derivative with an alcohol in the presence of an acid catalyst. The invention further relates to a process for preparing an N-alkoxyphenyl protected β-amino acid ester derivative comprising treating a N-phenylisoxazolidin-5-one derivative with an alcohol in the presence of an acid catalyst.

BACKGROUND

N-Phenylisoxazolidin-5-one derivatives may be used as intermediates in the preparation of β-amino acid esters, which can be further converted into other biologically important compounds, for example, β-amino acids. β-Amino acids possess biologically important properties, occur in natural products, and are the building blocks to several bioactive compounds.

The preparation of N-phenylisoxazolidin-5-one derivatives may involve carbon-nitrogen (C—N) bond forming reactions. Catalytic methods for C—N bond formation have been reported and have been applied in organic synthesis, including in the preparation of pharmaceuticals and natural products.

Organocatalytic reactions for forming C—N bonds are of interest, as these reactions may avoid the use of toxic and/or expensive metal catalysts. Examples of organocatalytic C—N bond formation reactions, including proline-catalyzed direct α-aminations of carbonyl compounds, have been reported. N-Nitroso aldol reaction of enamines selectively forming N-hydroxyaminoketones have also been reported (see, for example, Yamamoto, H. and Momiyama, N. *J. Am. Chem. Soc.* 2005, 127, 1080; Momiyama, N.; Yamamoto, Y.; Yamamoto, H. *J. Am. Chem. Soc.* 2007, 129, 1190). The enantioselective conjugate addition of N-silyloxycarbamates to enals using imidazolidinone catalysts has been used to obtain enantio-enriched β-amino aldehydes. The reaction of enals and N-protected hydroxylamine in the presence of chiral pyrrolidine catalysts, forming 5-hydroxyisoxazolidines that are further converted to the corresponding β-amino acids or γ-amino alcohols, has been reported.

In addition to C—N bond formation, organocatalytic reactions for forming carbon-carbon (C—C) bonds have been reported. For example, NHC-catalyzed activation of carbonyl compounds has been reported as a potential method for metal-free C—C bond forming reactions via the nucleophilic "Breslow intermediate", or the homoenolate equivalent species (see, for example, Sohn, S. S.; Rosen, E. L.; Bode, J. F. *J. Am. Chem. Soc.* 2004, 126, 14370; Burstein, C. and Glorius, F. *Angew. Chem., Int. Ed.* 2004, 43, 6205). The ability of thiamine-dependent enzymes to convert aromatic nitroso compounds into hydroxamic acids has been reported.

Additional approaches to synthesizing N-phenylisoxazolidin-5-one derivatives and β-amino acid ester derivatives involving readily available reactants and catalysts are desirable.

SUMMARY

In one broad aspect of the present invention, there is provided a process for preparing a N-phenylisoxazolidin-5-one derivative comprising reacting an α,β-unsaturated aldehyde with nitrosobenzene in the presence of a N-heterocyclic carbene (NHC) catalyst.

In an embodiment of the present invention, there is provided a process for preparing a N-phenylisoxazolidin-5-one derivative represented by the formula (I):

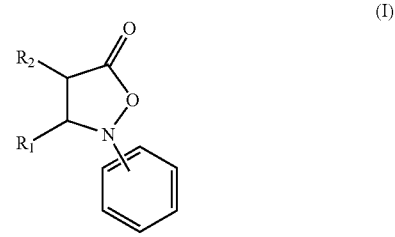

wherein:
$R_1$ is a hydrogen atom, a halogen atom, a nitrile group, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different, a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{2-6}$ alkynyl group which may be substituted with one or more substituents which are the same or different, a 4- to 10-membered non-aromatic heterocyclic group containing one or more heteroatoms which are independently nitrogen, sulfur or oxygen and which group may be substituted with one or more substituents which are the same or different, a 5- to 14-membered aromatic heterocyclic group containing one or more heteroatoms which are independently nitrogen, sulfur or oxygen and which group may be substituted with one or more substituents which are the same or different or a $C_{1-6}$ alkoxycarbonyl group which may be substituted with one or more substituents which are the same or different; and
$R_2$ is a hydrogen atom, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different or a $C_{3-8}$ cycloalkenyl group which may be substituted with one or more substituents which are the same or different, which process comprises reacting an α,β-unsaturated aldehyde represented by the formula (II):

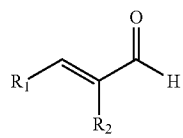

(II)

wherein each of $R_1$ and $R_2$ is as defined above, with nitrosobenzene in the presence of a NHC catalyst.

In an exemplary embodiment of the present invention, $R_2$ is hydrogen.

In a further aspect of the present invention, there is provided a process for preparing a N-phenylisoxalidin-5-one derivative represented by the formula:

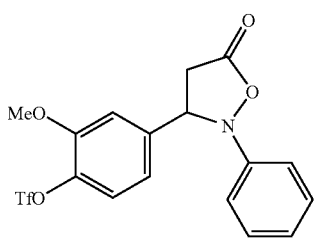

comprising reacting an α,β-unsaturated aldehyde represented by the formula:

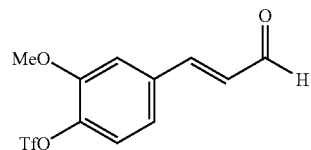

with nitrosobenzene in the presence of a NHC catalyst.

In another broad aspect of the present invention, there is provided a process for preparing an N-alkoxyphenyl protected β-amino acid ester derivative comprising reacting an α,β-unsaturated aldehyde with nitrosobenzene in the presence of a N-heterocyclic carbene (NHC) catalyst to form a N-phenylisoxazolidin-5-one derivative and then treating the N-phenylisoxazolidin-5-one derivative with an alcohol in the presence of an acid catalyst.

In an embodiment of the present invention, there is provided a process for preparing an N-alkoxyphenyl protected β-amino acid ester derivative represented by the formula (IV):

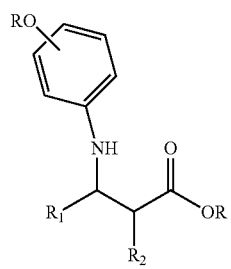

(IV)

wherein each of $R_1$ and $R_2$ is as defined above and $R_8$ is a $C_{1-6}$ alkyl group, which process comprises:

(a) reacting an α,β-unsaturated aldehyde represented by the formula (II):

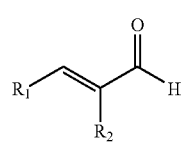

(II)

wherein each of $R_1$ and $R_2$ is as defined above, with nitrosobenzene in the presence of a NHC catalyst to form a N-phenylisoxazolidin-5-one derivative represented by the formula (I):

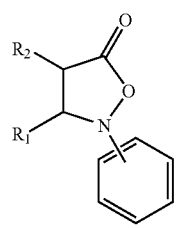

(I)

wherein each of $R_1$ and $R_2$ is as defined above; and (b) then treating the N-phenylisoxazolidin-5-one derivative with an alcohol represented by the formula $R_8OH$ wherein $R_8$ is as defined above, in the presence of an acid catalyst.

In an exemplary embodiment of the present invention, the alcohol is methanol.

In an exemplary embodiment of the present invention, the N-alkoxyphenyl protected β-amino acid ester derivative is an N-p-alkoxyphenyl protected β-amino acid ester derivative.

In still another aspect of the present invention, there is provided a process for preparing an N-alkoxyphenyl protected β-amino acid ester derivative represented by the formula:

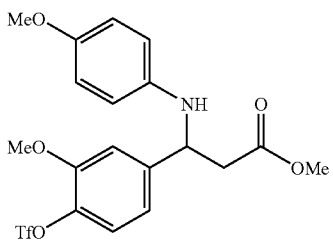

comprising reacting an α,β-unsaturated aldehyde represented by the formula:

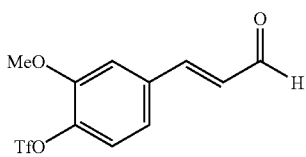

with nitrosobenzene in the presence of a NHC catalyst to form a N-phenylisoxalidin-5-one derivative represented by the formula:

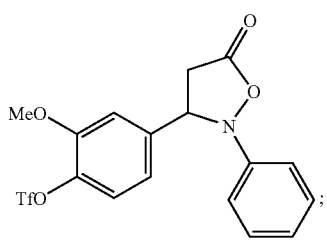

and then treating the N-phenylisoxalidin-5-one derivative with methanol in the presence of an acid catalyst.

In a further broad aspect of the present invention, there is provided a process for preparing an N-alkoxyphenyl protected β-amino acid ester derivative comprising treating a N-phenylisoxazolidin-5-one derivative with an alcohol in the presence of an acid catalyst.

In an embodiment of the present invention, there is provided a process for preparing an N-alkoxyphenyl protected β-amino acid ester derivative represented by the formula (IV):

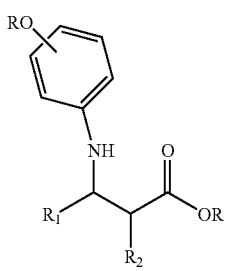

wherein each of $R_1$, $R_2$ and $R_8$ is as defined above, which process comprises treating a N-phenylisoxazolidin-5-one derivative represented by the formula (I):

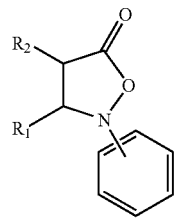

wherein each of $R_1$ and $R_2$ is as defined above, with an alcohol represented by the formula $R_8OH$ wherein $R_8$ is as defined above, in the presence of an acid catalyst.

In an exemplary embodiment of the present invention, the alcohol is methanol.

In an exemplary embodiment of the present invention, the N-alkoxyphenyl protected β-amino acid ester derivative is an N-p-alkoxyphenyl protected β-amino acid ester derivative.

In still a further aspect of the present invention, there is provided a process for preparing an N-alkoxyphenyl protected β-amino acid ester derivative represented by the formula:

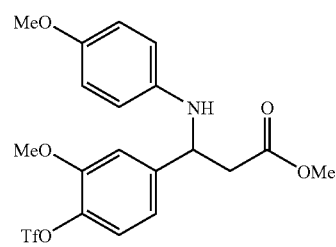

comprising treating a N-phenylisoxalidin-5-one derivative represented by the formula:

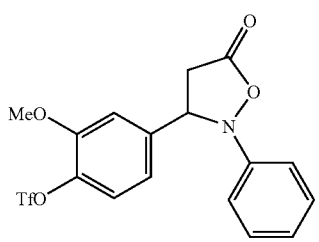

with methanol in the presence of an acid catalyst.

DETAILED DESCRIPTION

I. Process for Preparing N-Phenylisoxazolidin-5-One Derivative

In an embodiment of the process of the present invention to prepare a N-phenylisoxazolidin-5-one derivative, an α,β-unsaturated aldehyde may be reacted with nitrosobenzene in the presence of a NHC catalyst.

A. α,β-Unsaturated Aldehyde

The α,β-unsaturated aldehyde that may be used in the present invention is not particularly limited.

In an embodiment of the present invention, the α,β-unsaturated aldehyde may be, for example, and without limitation, an alkyl, alkenyl, alkynyl, cycloalkyl, cycloalkenyl, aryl, arylalkyl, arylalkenyl, arylalkynyl, heterocyclic or alkoxycarbonyl α,β-unsaturated aldehyde which may be substituted with one or more substituents which are the same or different.

In an embodiment of the present invention, the α,β-unsaturated aldehyde may be represented by, for example, and without limitation, a compound of the formula (II):

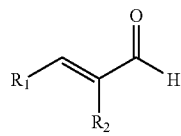

(II)

wherein:
$R_1$ is a hydrogen atom, a halogen atom, a nitrile group, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different, a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{2-6}$ alkynyl group which may be substituted with one or more substituents which are the same or different, a 4- to 10-membered non-aromatic heterocylic group containing one or more heteroatoms, which are independently nitrogen, sulfur or oxygen and which group may be substituted with one or more substituents which are the same or different, a 5- to 14-membered aromatic heterocyclic group containing one or more heteroatoms which are independently nitrogen, sulfur or oxygen and which group may be substituted with one or more substituents which are the same or different or a $C_{1-6}$ alkoxycarbonyl group which may be substituted with one or more substituents which are the same or different; and
$R_2$ is a hydrogen atom, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different or a $C_{3-8}$ cycloalkenyl group which may be substituted with one or more substituents which are the same or different.

The $C_{1-6}$ alkyl group of the $C_{1-6}$ alkyl group which may be substituted, may be, for example, and without limitation, any straight or branched alkyl, for example, methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl or 3-methylpentyl. The $C_{1-6}$ alkyl group may be, for example, and without limitation, optionally interrupted with one or more heteroatoms which are independently nitrogen, sulfur or oxygen.

The $C_{2-6}$ alkenyl group of the $C_{2-6}$ alkenyl group which may be substituted, may be, for example, and without limitation, any straight or branched alkenyl, for example, vinyl, allyl, isopropenyl, 1-propene-2-yl, 1-butene-1-yl, 1-butene-2-yl, 1-butene-3-yl, 2-butene-1-yl or 2-butene-2-yl. The $C_{2-6}$ alkenyl group may be, for example, and without limitation, optionally interrupted with one or more heteroatoms which are independently nitrogen, sulfur or oxygen.

The $C_{2-6}$ alkynyl group of the $C_{2-6}$ alkynyl group which may be substituted, may be, for example, and without limitation, any straight or branched alkynyl, for example, ethynyl, propynyl, butynyl, pentynyl or hexynyl. The $C_{2-6}$ alkynyl group may be, for example, and without limitation, optionally interrupted with one or more heteroatoms which are independently nitrogen, sulfur or oxygen.

The $C_{3-8}$ cycloalkyl group of the $C_{3-8}$ cycloalkyl group which may be substituted, may be, for example, and without limitation, cyclopropanyl, cyclobutanyl, cyclopentanyl, cyclohexanyl or cycloheptanyl.

The $C_{3-8}$ cycloalkenyl group of the $C_{3-8}$ cycloalkenyl group which may be substituted, may be, for example, and without limitation, cyclopropenyl, cyclobutenyl, cyclopentenyl, cyclohexenyl or cycloheptenyl.

The $C_{6-14}$ aryl group of the $C_{6-14}$ aryl group which may be substituted, may be, for example, and without limitation, phenyl, pentalenyl, indenyl, naphthyl, azulenyl, heptalenyl, benzocyclooctenyl or phenanthrenyl.

The $C_{6-14}$ aryl-$C_{1-6}$ alkyl group of the $C_{6-14}$ aryl-$C_{1-6}$ alkyl group which may be substituted, may be, for example, and without limitation, a $C_{1-6}$ alkyl group as defined anywhere above having a $C_{6-14}$ aryl group as defined anywhere above as a substituent.

The $C_{6-14}$ aryl-$C_{2-6}$ alkenyl group of the $C_{6-14}$ aryl-$C_{2-6}$ alkenyl group which may be substituted, may be, for example, and without limitation, a $C_{2-6}$ alkenyl group as defined anywhere above having a $C_{6-14}$ aryl group as defined anywhere above as a substituent.

The $C_{6-14}$ aryl-$C_{2-6}$ alkynyl group of the $C_{6-14}$ aryl-$C_{2-6}$ alkynyl group which may be substituted, may be, for example, and without limitation, a $C_{2-6}$ alkynyl group as defined anywhere above having a $C_{6-14}$ aryl group as defined anywhere above as a substituent.

The 4- to 10-membered non-aromatic heterocyclic group containing one or more heteroatoms which are independently nitrogen, sulfur or oxygen of the 4- to 10-membered non-aromatic heterocyclic group containing one or more heteroatoms which are independently nitrogen, sulfur or oxygen and which group may be substituted, may contain, for example, and without limitation, from 1 to 4 heteroatoms which are independently nitrogen, sulfur or oxygen. The 4- to 10-membered non-aromatic heterocyclic group containing one or more heteroatoms which are independently nitrogen, sulfur or oxygen may be, for example, and without limitation, pyrrolidinyl, pyrrolinyl, piperidinyl, piperazinyl, imidazolinyl, pyrazolidinyl, imidazolydinyl, morpholinyl, tetrahydropyranyl, azetidinyl, oxetanyl, oxathiolanyl, phthalimide or succinimide.

The 5- to 14-membered aromatic heterocyclic group containing one or more heteroatoms which are independently nitrogen, sulfur or oxygen of the 5- to 14-membered aromatic heterocyclic group containing one or more heteroatoms which are independently nitrogen, sulfur or oxygen and which group may be substituted, may contain, for example, and without limitation, from 1 to 4 heteroatoms which are independently nitrogen, sulfur or oxygen. The 5- to 14-membered aromatic heterocyclic group containing one or more heteroatoms which are independently nitrogen, sulfur or oxygen may be, for example, and without limitation, pyrrolyl, pyridinyl, pyridazinyl, pyrimidinyl, pyrazinyl, imidazolyl, thiazolyl or oxazolyl.

The $C_{1-6}$ alkoxycarbonyl group of the $C_{1-6}$ alkoxycarbonyl group which may be substituted, may be, for example, and without limitation, methoxycarbonyl, ethoxycarbonyl, n-propoxycarbonyl, i-propoxy carbonyl, sec-propoxycarbonyl, n-butoxycarbonyl, i-butoxycarbonyl, 1,2-dimethylpropoxycarbonyl or 2-ethylpropoxycarbonyl.

Each of the $C_{1-6}$ alkyl, $C_{2-6}$ alkenyl, $C_{2-6}$ alkynyl, $C_{3-8}$ cycloalkyl, $C_{3-8}$ cycloalkenyl, $C_{6-14}$ aryl, $C_{6-14}$ aryl-$C_{1-6}$ alkyl, $C_{6-14}$ aryl-$C_{2-6}$ alkenyl, $C_{6-14}$ aryl-$C_{2-6}$ alkynyl, 4- to 10-membered non-aromatic heterocylic, 5- to 14-membered aromatic heterocyclic and $C_{1-6}$ alkoxycarbonyl groups may be substituted with one or more substituents which are the same or different. In an embodiment of the present invention, each of the above-mentioned groups may be, for example, and without limitation, substituted with one to three substituents which are the same or different.

The one or more substituents which are the same or different for each of the above-mentioned groups may be, for example, and without limitation, a halogen atom, a hydroxyl group, a thiol group, a nitro group, a nitrile group, a cyano group, a $C_{1-6}$ alkyl, $C_{2-6}$ alkenyl or $C_{2-6}$ alkynyl group which may be substituted with a halogen atom, a $C_{3-8}$ cycloalkyl or $C_{3-8}$ cycloalkenyl group which may be substituted, a $C_{6-14}$ aryl group which may be substituted, a 4- to 10-membered non-aromatic heterocylic group containing 1 to 4 heteroatoms which are independently nitrogen, oxygen or sulfur and which group may be substituted, a 5- to 14-membered aromatic heterocylic group containing 1 to 4 heteroatoms which are independently nitrogen, oxygen or sulfur and which group may be substituted, a $C_{1-6}$ alkoxy group which may be substituted, a $C_{3-8}$ cycloalkoxy group which may be substituted, a $C_{1-6}$ alkylthio, $C_{2-6}$ alkenylthio or $C_{2-6}$ alkynylthio group which may be substituted, a $C_{3-8}$ cycloalkylthio or $C_{3-8}$ cycloalkenylthio group which may be substituted, a $C_{6-14}$ aryloxy group which may be substituted, a 4- to 10-membered non-aromatic heterocycle-oxy group which may be substituted, a 5- to 14-membered aromatic heterocycle-oxy group which may be substituted, a $C_{6-14}$ arylthio group which may be substituted, a 4- to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a $C_{1-6}$ imidoyl group, a carbonyl group which is substituted, a carbonyl-oxy group which is substituted, a carboxy group, a carbamoyl group which may be substituted, a $C_{1-4}$ alkylenedioxy group, a sulfinyl group which is substituted, a sulfonyl which is substituted with a trifluoromethyl group, a $C_{1-6}$ alkoxycarbonyl group, a $C_{1-6}$ alkylsulfonyl group, an oxo group or a $C_{1-6}$ alkoxyimino group.

In an embodiment of the present invention, $R_1$ is, for example, a $C_{1-6}$ alkoxycarbonyl group or a $C_{6-14}$ aryl group which may be substituted with 1 to 3 substituents which are independently nitro, trifluoromethyl, trifluoromethylsulfonyl, methoxy or methoxycarbonyl.

In an exemplary embodiment of the present invention, $R_2$ is a hydrogen atom.

B. Nitrosobenzene

Nitrosobenzene may be represented by the formula (III):

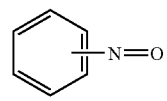

(III)

C. NHC Catalyst

The NHC catalyst of the present invention is not particularly limited.

In an embodiment of the present invention, the NHC catalyst may be derived from, for example, and without limitation, an imidazolium salt.

In an embodiment of the present invention, the NHC catalyst may be derived from, for example, and without limitation, an imidazolium salt represented by the formula (V):

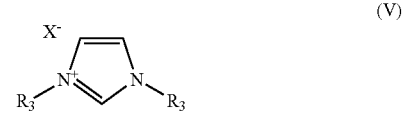

(V)

wherein $R_3$ may be, for example, and without limitation, phenyl (Ph), i-propyl ($^i$Pr), mesityl (Mes) or 2,6-diisopropylphenyl (2,6-$^i$Pr-Ph); and $X^-$ may be, for example, and without limitation, $Br^-$, $BF_4^-$ or $Cl^-$.

In an embodiment of the present invention, the NHC catalyst may be derived from, for example, and without limitation, an imidazolium salt represented by the formula:

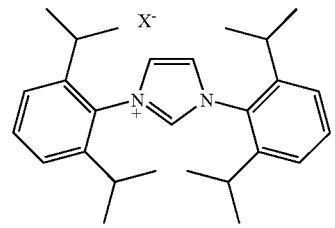

wherein $X^-$ may be, for example, and without limitation, $Br^-$, $BF_4^-$ or $Cl^-$. In an embodiment, $X^-$ is, for example, $Cl^-$.

In an embodiment of the present invention, the NHC catalyst may be derived from, for example, and without limitation, an imidazolium salt represented by the formula:

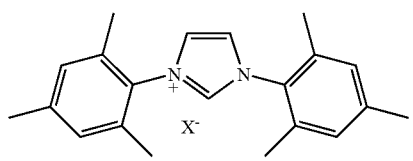

wherein $X^-$ may be, for example, and without limitation, $Br^-$, $BF_4^-$ or $Cl^-$. In an embodiment, $X^-$ is, for example, $Cl^-$.

In an embodiment of the present invention, the NHC catalyst may be derived from, for example, and without limitation, an imidazolium salt represented by the formula:

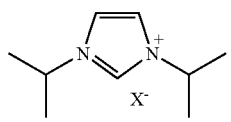

wherein X⁻ may be, for example, and without limitation, Br⁻, BF₄⁻ or Cl⁻. In an embodiment, X⁻ is, for example, BF₄⁻.

In an embodiment of the present invention, the NHC catalyst may be derived from, for example, and without limitation, an imidazolium salt represented by the formula:

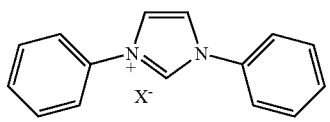

wherein X⁻ may be, for example, and without limitation, Br⁻, BF₄⁻ or Cl⁻. In an embodiment, X⁻ is, for example, Br⁻.

In an embodiment of the present invention, the NHC catalyst may be derived from, for example, and without limitation, an imidazolium salt represented by the formula:

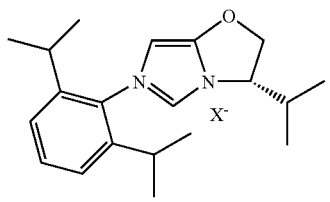

wherein X⁻ may be, for example, and without limitation, trifluoromethylsulfonate (⁻OTf), Br⁻, BF₄⁻ or Cl⁻. In an embodiment, X⁻ is, for example, ⁻OTf.

In an embodiment of the present invention, the NHC catalyst may be derived from, for example, and without limitation, an imidazolium salt represented by the formula:

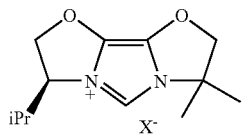

wherein X⁻ may be, for example, and without limitation, Br⁻, BF₄⁻ or Cl⁻.

In an embodiment of the present invention, the NHC catalyst may be derived from, for example, and without limitation, an imidazolium salt represented by the formula:

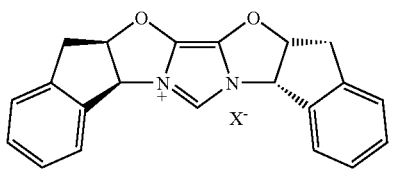

wherein X⁻ may be, for example, and without limitation, Br⁻, BF₄⁻ or Cl⁻.

In an embodiment of the present invention, the NHC catalyst may be derived from, for example, and without limitation, an imidazolium salt represented by the formula:

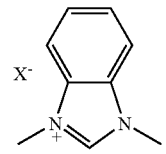

wherein X⁻ may be, for example, and without limitation, Br⁻, BF₄⁻ or Cl⁻.

In an embodiment of the present invention, the NHC catalyst may be derived from, for example, and without limitation, an imidazolium salt represented by the formula:

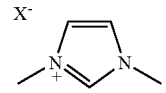

wherein X⁻ may be, for example, and without limitation, Br⁻, BF₄⁻ or Cl⁻.

In an embodiment of the present invention, the NHC catalyst may be derived from, for example, and without limitation, an imidazolium salt represented by the formula:

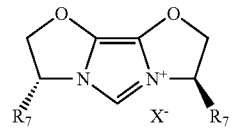

wherein $R_7$ may be, for example, and without limitation, $^i$Pr and t-Bu; and X⁻ may be, for example, and without limitation, Br⁻, BF₄⁻ or Cl⁻.

In an embodiment of the present invention, the NHC catalyst may be derived from, for example, and without limitation, an imidazolium salt represented by the formula:

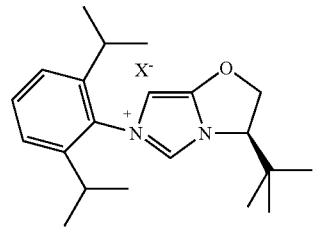

wherein X⁻ may be, for example, and without limitation, trifluoromethylsulfonate (⁻OTf), Br⁻, BF₄⁻ or Cl⁻. In an embodiment, X⁻ is, for example, ⁻OTf.

In an embodiment of the present invention, the NHC catalyst may be derived from, for example, and without limitation, an imidazolium salt represented by the formula (VI):

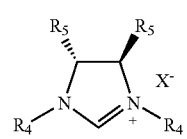

(VI)

wherein $R_4$ may be, for example, and without limitation, 2,6-$^i$Pr-Ph; $R_5$ may be, for example, and without limitation, hydrogen or Ph; and X⁻ may be, for example, and without limitation, Cl⁻.

In an embodiment of the present invention, the NHC catalyst may be derived from, for example, and without limitation, an imidazolium salt represented by the formula (VII):

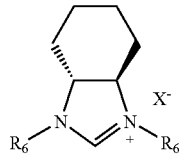

(VII)

wherein $R_6$ may be, for example, and without limitation, 2,6-$^i$Pr-Ph and $X^-$ may be, for example, and without limitation, $Cl^-$.

D. N-Phenylisoxazolidin-5-one Derivative

In an embodiment, the N-phenylisoxazolidin-5-one derivative that may be prepared in the present invention, may be represented by, for example, and without limitation, a compound of the formula (I):

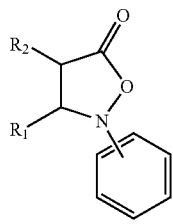

(I)

wherein each of $R_1$ and $R_2$ is as defined anywhere above.

E. Preparation of N-Phenylisoxazolidin-5-one Derivative

An embodiment of the process for preparing the N-phenylisoxazolidin-5-one derivative of the present invention may be represented by, for example, and without limitation, the following scheme:

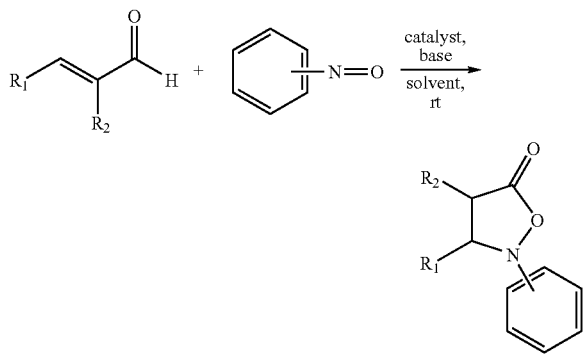

wherein each of $R_1$ and $R_2$ is as defined anywhere above.

Without being bound by theory, as represented in the following scheme by way of example, and without limitation, it is believed that the nitroso compound can act as an electrophile, forming C—N bonds leading to amides or β-amino acid derivatives.

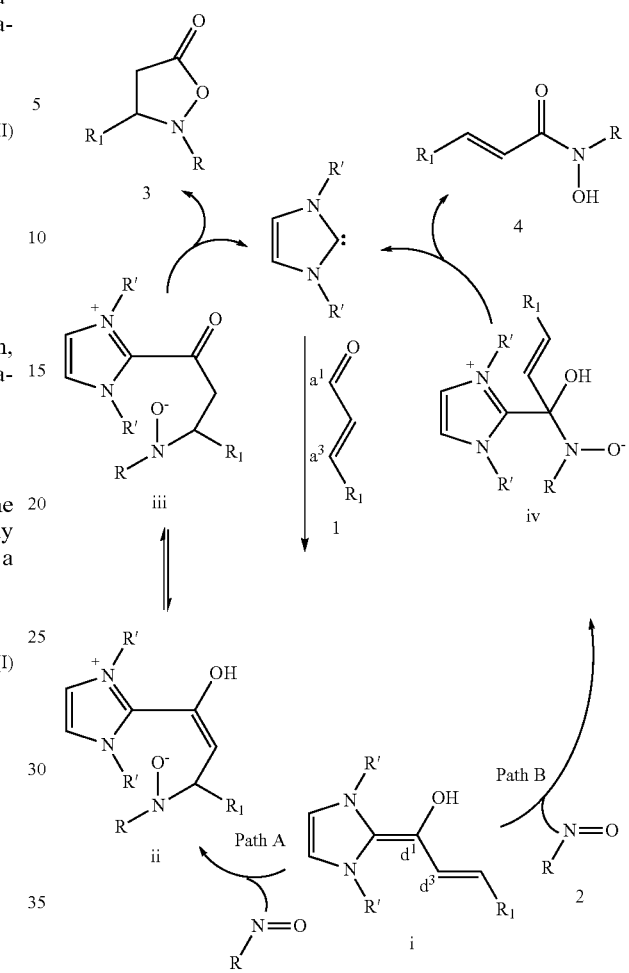

wherein in the scheme R is phenyl, $R_1$ is as defined anywhere above and R' is a hydrocarbon group, including those groups defined for $R_1$ as above.

It is believed that coupling of the nitroso compound 2 with the homoenolate equivalent i ($d^3$ nucleophile) forms intermediate nitroxide species ii and iii (Path A). The nitroxide species iii can then attack the carbonyl group of the activated carboxylate intramolecularly, leading to formation of the isoxazolidin-5-one 3, returning the carbene catalyst back for further turnovers. Potential competing reactions are believed to be the reaction of the $d^1$ nucleophile i with the nitroso compound 2 to form the N-hydroxycinnamamide 4 (Path B) and the self-condensation of the enal.

In an embodiment of the present invention, the α,β-unsaturated aldehyde, nitrosobenzene and the NHC catalyst may be, for example, reacted in the presence of a suitable base. The base is not particularly limited and suitable bases would be understood to and can be determined by those of ordinary skill in the art. In an embodiment of the present invention, the base may be, for example, and without limitation, 1,8-diazabicyclo[5.4.0]undec-7-ene (DBU), potassium tert-butoxide (KO$^t$Bu), sodium bis(trimethylsilyl)amide, potassium bis(t-rimethylsilyl) amide, lithium tetramethylpiperidine or sodium tert-butoxide. In an embodiment of the present invention, the base is, for example, 1,8-diazabicyclo[5.4.0]undec-7-ene or potassium tert-butoxide.

In an embodiment of the present invention, the reaction may be, for example, carried out in the presence of a suitable solvent. The solvent is not particularly limited and suitable solvents would be understood to and can be determined by those of ordinary skill in the art. In an embodiment of the present invention, the solvent may be, for example, and without limitation, dichloromethane ($CH_2Cl_2$) or tetrahydrofuran (THF).

The amounts of the α,β-unsaturated aldehyde and nitrosobenzene that may be used in the present invention are not particularly limited. Suitable amounts of the α,β-unsaturated aldehyde and nitrosobenzene would be understood to and can be determined by those of ordinary skill in the art. For example, and without limitation, those of ordinary skill in the art would understand that the α,β-unsaturated aldehyde and nitrosobenzene may be reacted according to their stoichiometric ratio.

The amount of the NHC catalyst that may be used in the present invention is not particularly limited. Suitable amounts of the NHC catalyst would be understood to and could be determined by those of ordinary skill in the art. In an embodiment of the present invention, the amount of the NHC catalyst may be, for example, and without limitation, less than 20 mol %, for example, and without limitation from 10 to 20 mol %, and including any specific value within this range.

The reaction time is not particularly limited and suitable reaction times would be understood to and can be determined by those of ordinary skill in the art. In an embodiment of the present invention, the reaction time may be, for example, and without limitation, less than 12 hours, for example, and without limitation, from 1 to 12 hours, and including any specific time within this range, such as, for example, and without limitation, from 1 to 6 hours or from 1 to 3 hours.

The reaction temperature is not particularly limited and suitable reaction temperatures would be understood to and can be determined by those of ordinary skill in the art. In an embodiment of the present invention, the reaction temperature may be, for example, and without limitation, room temperature.

In an embodiment of the present invention, the N-phenylisoxazolidin-5-one derivative may be, for example, isolated and/or purified. Suitable isolation and/or purification methods would be understood to and can be determined by those of ordinary skill in the art. For example, and without limitation, those of ordinary skill in the art would understand that the N-phenylisoxazolidin-5-one derivative may be isolated and/or purified by chromatographic methods.

Non-limiting examples of one process of the present invention are described in more detail herein.

F. Examples

A number of the N-phenylisoxazolidin-5-one derivatives were not isolated due to potential decarboxylation and further hydrolysis. Formation of the derivatives was monitored separately by $^1H$ nuclear magnetic resonance (NMR) studies.

In general, for the $^1H$ NMR studies, the base (0.10 mmol) was added under argon to a solution of α,β-unsaturated aldehyde (0.10 mmol), nitrosobenzene (0.11 mmol) and the catalyst (0.02 mmol) in the corresponding deuterated solvent (2 mL). The reaction mixture was stirred at room temperature for 1-3 h. The $^1H$ NMR spectra were recorded directly.

3-(4-Nitrophenyl)-2-phenylisoxazolidin-5-one was isolated and further studied by $^{13}C$ NMR.

$^1H$ and $^{13}C$ NMR spectra were obtained using a Brucker™ AV-400 (400 MHz) spectrometer. Chemical shifts were reported in ppm from tetramethylsilane with the solvent resonance as the internal standard. Data were reported in the following order: chemical shift in ppm (δ) (multiplicity were indicated by br (broadened), s (singlet), d (doublet), t (triplet), q (quartet), m (multiplet)); coupling constants (J, Hz); integration; assignment.

The following compounds were prepared and studied in accordance with the above method.

2,3-Diphenylisoxazolidin-5-one

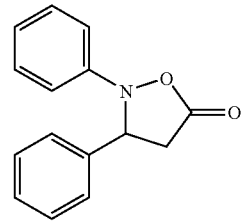

$^1H$ NMR (400 MHz, $CDCl_3$): δ 7.40-7.00 (m, 10H, Ar—H), 4.77 (dd, J=7.6, 9.6 Hz, 1H, CH), 3.13 (dd, J=7.6, 17.3 Hz, 1H, $CH_2$), 2.94 (dd, J=9.6, 17.3 Hz, 1H, $CH_2$). MS (ESI): m/z 239 ($M^{3o}$), 196, 131, 120, 104.

3-(4-Nitrophenyl)-2-phenylisoxazolidin-5-one

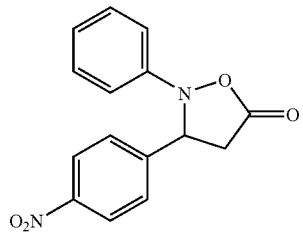

$^1H$ NMR (400 MHz, $CDCl_3$): δ 8.24 (AB, d, $J_{AB}$=8.8 Hz, 2H, Ar—H), 7.62 (AB, d, $J_{AB}$=8.8 Hz, 2H, Ar—H), 7.19-7.05 (m, 4H, Ar—H), 6.98-6.95 (m, 1H, Ar—H), 5.14 (dt, J=2.5, 6.0 Hz, 1H, CH), 3.12 (dd, J=6.0, 12.9 Hz, 1H, $CH_2$), 2.81 (dd, J=6.0, 12.9 Hz, 1H, $CH_2$). $^{13}C$ NMR (100 MHz, $CDCl_3$): δ 167.8 (Cq, CO), 149.3, 144.9, 135.2 (Cq), 126.6, 124.3, 124.2, 122.8, 120.7 (C—Ar), 62.5 (CH), 38.8 ($CH_2$).

3-(2-Nitrophenyl)-2-phenylisoxazolidin-5-one

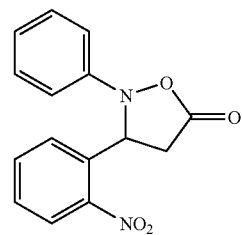

$^1H$ NMR (400 MHz, $CDCl_3$): δ 8.00-6.90 (m, 9H, Ar—H), 5.54 (dd, J=5.8, 8.7 Hz, 1H, CH), 3.49 (dd, J=8.7, 17.9 Hz, 1H, $CH_2$), 2.68 (dd, J=5.8, 17.9 Hz, 1H, $CH_2$). m/z 284 ($M^+$), 266, 249, 224, 176, 130, 120, 108, 91, 79.

2-Methoxy-4-(5-oxo-2-phenylisoxazolidin-3-yl)phenyl trifluoromethanesulfonate

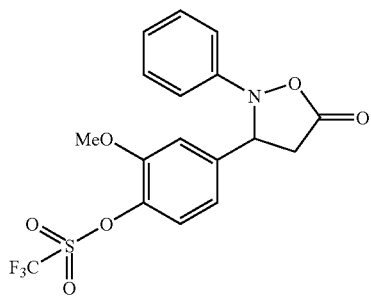

$^1$H NMR (400 MHz, CDCl$_3$): δ 7.70-7.00 (m, 8H, Ar—H), 4.84 (t, J=8.0 Hz, 1H, CH), 3.84 (s, 3H, OCH$_3$), 3.20 (dd, J=8.0, 17.3 Hz, 1H, CH$_2$), 2.92 (dd, J=8.9, 17.3 Hz, 1H, CH$_2$).

3-(4-(Trifluoromethyl)phenyl)-2-phenylisoxazolidin-5-one

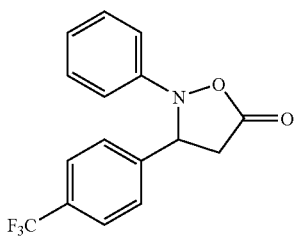

$^1$H NMR (400 MHz, CDCl$_3$): δ 7.59-7.00 (m, 9H, Ar—H), 4.87 (t, J=8.1 Hz, 1H, CH), 3.19 (dd, J=8.1, 17.3 Hz, 1H, CH$_2$), 2.90 (dd, J=9.0, 17.3 Hz, 1H, CH$_2$). MS (ESI) m/z 307 (M$^+$), 264, 199, 120, 109.

Ethyl 5-oxo-2-phenylisoxazolidine-3-carboxylate

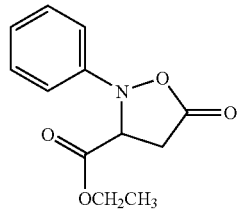

$^1$H NMR (400 MHz, CDCl$_3$): δ 7.50-7.00 (m, 5H, Ar—H), 4.62 (dd, J=4.9, 7.5 Hz, 1H, CH), 4.26 (q, J=7.0 Hz, 2H, OCH$_2$), 3.11 (m$_c$, 2H, CH$_2$), 1.29 (t, J=7.0 Hz, 3H, CH$_3$). MS (ESI): m/z 235 (M$^+$), 207, 162, 134, 120, 99.

Cinnamaldehyde and nitrosobenzene were observed to react in the presence of the NHC catalysts, forming 2,3-diphenylisoxazolidin-5-one. In, studies using different imidazolium and triazolium salts, it was observed that more sterically hindered imidazolium catalysts provided higher yields of the product (Table 1).

Azoxybenzene side-product was observed. By modifying reactions conditions in accordance with routine experiments, the amount of azoxybenzene can be minimized.

TABLE 1

Reaction Conditions for NHC-catalyzed Synthesis of N-Phenylisoxazolidin-5-one Derivatives

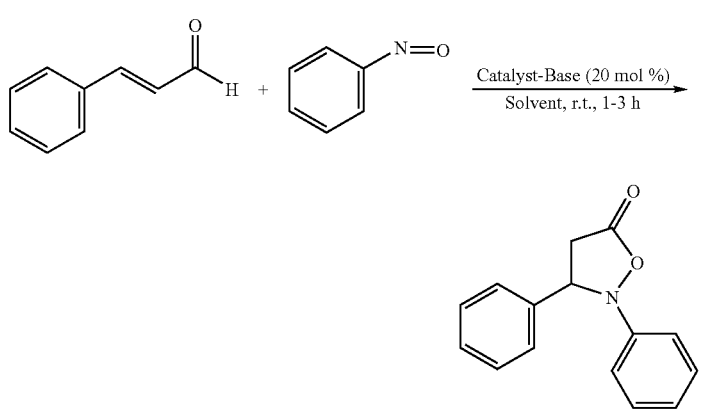

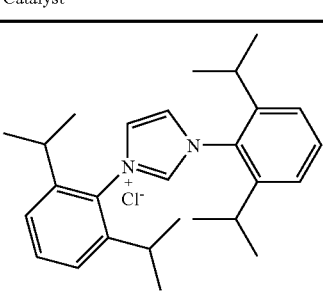

| entry | Catalyst | Solvent | base | yield, %$^a$ |
|---|---|---|---|---|
| 1 | (IPrCl) | THF | KO$^t$Bu | 80 |

TABLE 1-continued

| | | | | |
|---|---|---|---|---|
| 2 | (IMesCl) | THF | KO$^t$Bu | 60 |
| 3b | 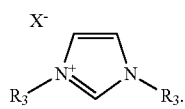 | THF | KO$^t$Bu | — |
| 4 | IprCl | CH$_2$Cl$_2$ | KO$^t$Bu | 82 |
| 5 | IprCl | Benzene | KO$^t$Bu | 50 |
| 6 | IprCl | CH$_2$Cl$_2$ | DBU$^c$ | 48 |

$^a$Yields determined by $^1$H NMR.
$^b$Exclusive formation of N-hydroxy-N-phenylcinnamamide was observed.
$^c$DBU = 1,8-diazabicyclo[5.4.0]undec-7-ene.

Experiments were also conducted using the following catalysts, all in the presence of THF and KO$^t$Bu, and forming 2,3-diphenylisoxazolidin-5-one in the following yields (%):

i)

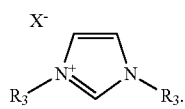

wherein R$_3$ = Ph and X$^-$ = Br$^-$; yield = 14% ii)

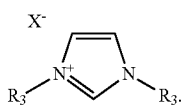

wherein R$_3$ = $^i$Pr and X$^-$ = BF$_4^-$; yield = 5% iii)

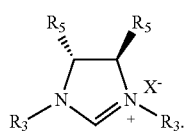

wherein R$_4$ = 2,6-$^i$Pr-Ph, R$_5$ = H and X$^-$ = Cl$^-$; yield = 10% iv)

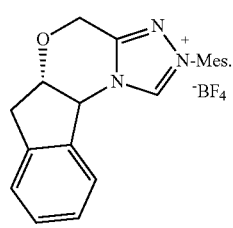

over 95% formation of N-hydroxy-N-phenylcinnamamide observed

II. Process for Preparing N-Alkoxyphenyl Protected β-Amino Acid Ester Derivative In an embodiment of the present invention, an α,β-unsaturated aldehyde may be reacted with nitrosobenzene in the presence of a NHC catalyst to form a N-phenylisoxalidin-5-one derivative, and then the N-phenylisoxalidin-5-one derivative may be treated with an alcohol in the presence of an acid catalyst to form an N-alkoxyphenyl protected β-amino acid ester derivative.

In an embodiment of the present invention, a Ar-phenylisoxalidin-5-one derivative may be treated with an alcohol in the presence of an acid catalyst to form an N-alkoxyphenyl protected β-amino acid ester derivative.

In an embodiment of the present invention, the N-alkoxyphenyl protected β-amino acid ester derivative may be deprotected.

A. α,β-Unsaturated Aldehyde, Nitrosobenzene, N-Phenylisoxalidin-5-one Derivative and NHC Catalyst The skilled person will appreciate that the α,β-unsaturated aldehyde, nitrosobenzene and the NHC catalyst as described above, which may be used for preparing the N-phenylisoxalidin-5-one derivative, may also be used for preparing the N-alkoxyphenyl protected β-amino acid ester derivative as described herein.

B. Alcohol

Suitable alcohols would be understood to and can be determined by those of ordinary skill in the art. In an embodiment of the present invention, the alcohol may be, for example, and without limitation, methanol, ethanol, propanol, butanol or pentanol.

In an embodiment of the present invention, the alcohol may be represented by, for example, and without limitation, the formula R$_8$OH wherein R$_8$ may be, for example, and without limitation, a C$_{1-6}$ alkyl group, including those groups defined for R$_1$ and R$_2$ above. In an embodiment of the present invention, R$_8$ may be, for example, methyl.

C. Acid Catalyst

The acid catalyst that may be used in the present invention is not particularly limited. Suitable acid catalysts would be understood to and can be determined by those of ordinary skill in the art. In an embodiment of the present invention, the acid catalyst may be, for example, and without limitation, perchloric acid.

D. N-Alkoxyphenyl Protected β-Amino Acid Ester Derivative

In an embodiment of the present invention, the N-alkoxyphenyl protected β-amino acid ester derivative may be represented by, for example, and without limitation, a compound of the formula (IV):

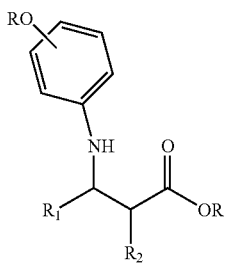

(IV)

wherein each of $R_1$, $R_2$ and $R_8$ is as defined anywhere above.

In an exemplary embodiment of the present invention, the N-alkoxyphenyl protected β-amino acid ester derivative may be, for example, a N-p-alkoxyphenyl protected β-amino acid ester derivative.

In an embodiment of the present invention, the N-alkoxyphenyl protected β-amino acid ester derivative may be, for example, a N-p-methoxyphenyl protected β-amino acid ester derivative.

E. Preparation of N-Alkoxyphenyl Protected β-Amino Acid Ester Derivative

An embodiment of the process of the present invention for preparing an N-alkoxyphenyl protected β-amino acid ester derivative may be represented by, for example, and without limitation, the following scheme:

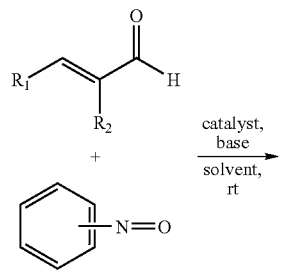

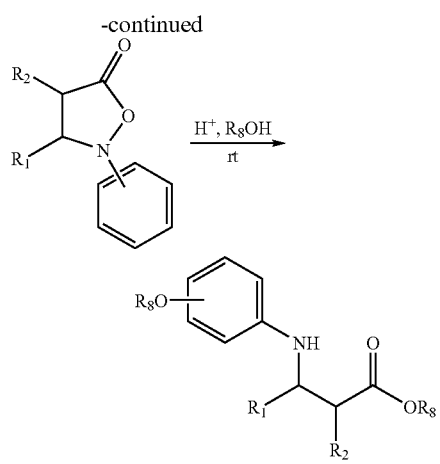

wherein each of $R_1$, $R_2$ and $R_8$ is as defined anywhere above.

An embodiment of the acid-catalyzed esterification, followed by the Bamberger-like rearrangement of the N-phenylisoxazolidin-5-one derivative for preparing the N-alkoxyphenyl protected β-amino acid ester derivative may be represented by, for example, and without limitation, the following scheme showing the acid-catalyzed ring opening and Bamberger-like rearrangement of 2,3-diphenylisoxazolidin-5-one.

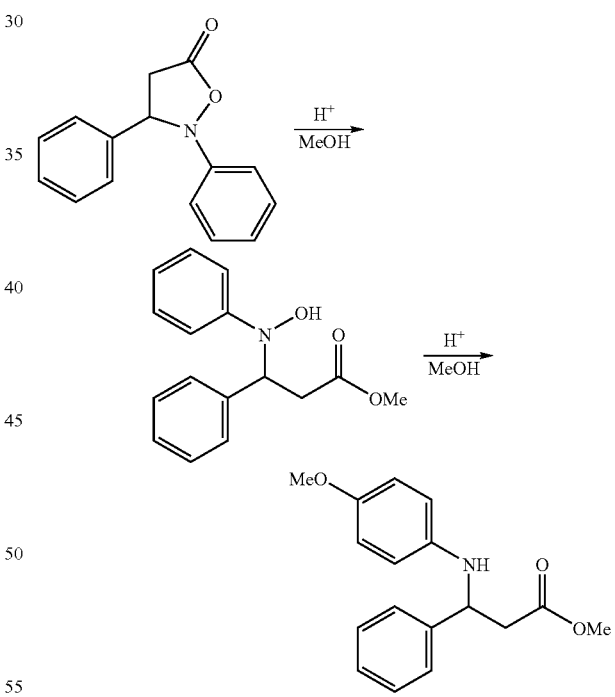

In an embodiment of the present invention, the process for preparing the N-alkoxyphenyl protected β-amino acid ester derivative may be, for example, and without limitation, a one-pot process.

In an embodiment of the present invention, the N-alkoxyphenyl protected β-amino acid ester derivative may be, for example, deprotected under mild oxidative conditions.

The process of the present invention may be used, for example, and without limitation, for the preparation of the natural product β-dihydroxyphenylalanine (β-DOPA), and may be represented by, for example, the following scheme:

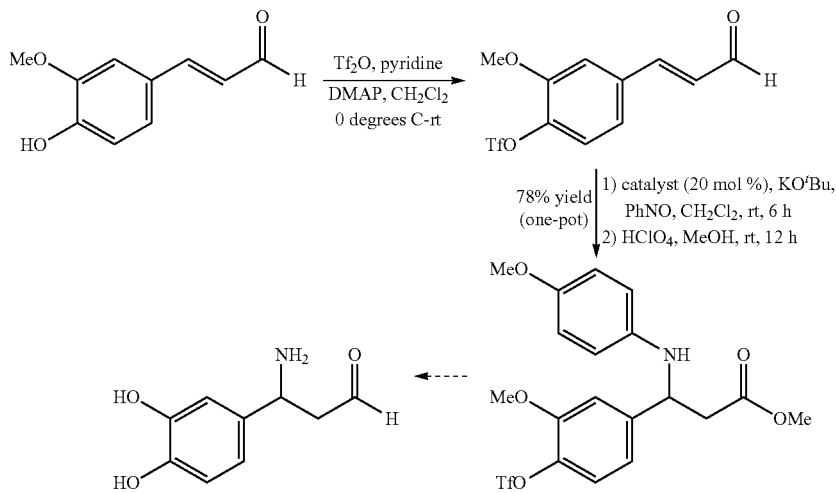

In an embodiment of the present invention, the α,β-unsaturated aldehyde, nitrosobenzene and the NHC catalyst may be, for example, reacted in the presence of a suitable base. The base is not particularly limited and suitable bases would be understood to and can be determined by those of ordinary skill in the art. In an embodiment of the present invention, the base may be, for example, and without limitation, 1,8-diazabicyclo[5.4.0]undec-7-ene, potassium tert-butoxide, sodium bis(trimethylsilyl)amide, potassium bis(trimethylsilyl) amide, lithium tetramethylpiperidine or sodium tert-butoxide. In an embodiment of the present invention, the base is, for example, 1,8-diazabicyclo[5.4.0]undec-7-ene or potassium tert-butoxide.

In an embodiment of the present invention, the reaction of the α,β-unsaturated aldehyde, nitrosobenzene and the NHC catalyst may be, for example, carried out in the presence of a suitable solvent. The solvent is not particularly limited and suitable solvents would be understood to and can be determined by those of ordinary skill in the art. In an embodiment of the present invention, the solvent may be, for example, and without limitation, dichloromethane or tetrahydrofuran.

The amounts of the α,β-unsaturated aldehyde and nitrosobenzene that may be used in the present invention are not particularly limited. Suitable amounts of the α,β-unsaturated aldehyde and nitrosobenzene would be understood to and can be determined by those of ordinary skill in the art. For example, and without limitation, those of ordinary skill in the art would understand that the α,β-unsaturated aldehyde and nitrosobenzene may be reacted according to their stoichiometric ratio.

The amount of the NHC catalyst that may be used in the present invention is not particularly limited. Suitable amounts of the NHC catalyst would be understood to and can be determined by those of ordinary skill in the art. In an embodiment of the present invention, the amount of the NHC catalyst may be, for example, and without limitation, less than 20 mol %, for example, and without limitation from 10 to 20 mol %, and including any specific value within this range.

The reaction time for the α,β-unsaturated aldehyde, nitrosobenzene and the NHC catalyst is not particularly limited and suitable reaction times would be understood to and can be determined by those of ordinary skill in the art. In an embodiment of the present invention, the reaction time may be, for example, and without limitation, less than 12 hours, for example, and without limitation, from 1 to 12 hours, and including any specific time within this range, such as, for example, and without limitation, from 1 to 6 hours or from 1 to 3 hours.

The reaction temperature for the α,β-unsaturated aldehyde, nitrosobenzene and the NHC catalyst is not particularly limited and suitable reaction temperatures would be understood to and can be determined by those of ordinary skill in the art. In an embodiment of the present invention, the reaction temperature may be, for example, and without limitation, room temperature.

The amount of the acid catalyst that may be used in the present invention is not particularly limited and suitable amounts of the acid catalyst would be understood to and can be determined by those of ordinary skill in the art.

The amounts of the N-phenylisoxalidin-5-one derivative and the alcohol that may be used are not particularly limited. Suitable amounts of the N-phenylisoxalidin-5-one derivative and the alcohol would be understood to and can be determined by those of ordinary skill in the art. For example, and without limitation, those of ordinary skill in the art would understand that a stoichiometric excess of the alcohol may be used.

The reaction time for the N-phenylisoxalidin-5-one derivative and the alcohol is not particularly limited and suitable reaction times for this step would be understood to and can be determined by those of ordinary skill in the art. In an embodiment of the present invention, the reaction time may be, for example, and without limitation, less than 24 hours, for example, and without limitation, from 1 to 24 hours, and including any specific time within this range, such as, for example, and without limitation, from 1 to 12 hours.

The reaction temperature for the N-phenylisoxalidin-5-one derivative and the alcohol is not particularly limited and suitable reaction temperatures would be understood to and can be determined by those of ordinary skill in the art. In an embodiment of the present invention, the reaction temperature may be, for example, and without limitation, room temperature.

In an embodiment of the present invention, the N-alkoxyphenyl protected β-amino acid ester derivative may be, for example, isolated and/or purified. Suitable isolation and/or purification methods would be understood to and can be determined by those of ordinary skill in the art. For example, and without limitation, those of ordinary skill in the art would understand that the N-alkoxyphenyl protected β-amino acid ester derivative may be isolated and/or purified by chromatographic methods.

The conditions for deprotecting the N-alkoxyphenyl protected β-amino acid ester derivative are not particularly limited and suitable conditions would be understood to and can be determined by those of ordinary skill in the art. In an embodiment of the present invention, the N-alkoxyphenyl protected β-amino acid ester derivative may be deprotected, for example, and without limitation, under mild oxidative conditions.

Non-limiting examples of one process of the present invention are described in more detail herein.

F. Examples

All reactions were performed in oven-dried (140° C.) or flame-dried glassware under an inert atmosphere of dry $N_2$ or argon. All solvents were anhydrous and purchased from Aldrich or Fluka.

KO$^t$Bu (0.1 mmol) was added under argon to a solution of α,β-unsaturated aldehyde (0.5 mmol), nitrosobenzene (0.51 mmol) and the catalyst (0.1 mmol) in dichloromethane (2 mL). The reaction mixture was stirred at room temperature for 1-3 h. The solvent was removed under vacuum, and the residue was diluted with methanol (5 mL), followed by addition of perchloric acid (3-5 drops). The mixture was stirred at room temperature overnight. The solvent was removed in vaccuo, and the residue was diluted with $CH_2Cl_2$ (5 mL) and saturated aqueous $NaHCO_3$ (10 mL). The aqueous layer was extracted with $CH_2Cl_2$ (10 mL×2). The combined organic layer was washed with saturated aqueous $NaHCO_3$ (10 mL) and then brine (10 mL), dried ($MgSO_4$), and concentrated. The pure product was obtained through flash silica gel column chromatography of the residue using hexane and ethyl acetate as the eluents.

In general, reactions were monitored by thin layer chromatography using 0.25 mm E. Merck silica gel coated glass plates (60E-254) with UV light to visualize the course of reaction. Flash column chromatography was performed using CombiFlash™ (ISCO, Inc.).

Chemical yields refer to pure isolated substances.

Gas chromatography-mass spectrometry (GC-MS) was conducted using Shimadzu™ GC-2010 coupled with GCMS-QP2010.

$^1$H and $^{13}$C nuclear magnetic resonance spectra were obtained using a Brucker™ AV-400 (400 MHz) spectrometer. Chemical shifts were reported in ppm from tetramethylsilane with the solvent resonance as the internal standard. Data were reported in the following order: chemical shift in ppm (δ) (multiplicity were indicated by br (broadened), (singlet), d (doublet), t (triplet), q (quartet), m (multiplet)); coupling constants (J, Hz); integration; assignment.

The following compounds were prepared in accordance with the above method.

Methyl 3-(4-methoxyphenylamino)-3-phenylpropanoate

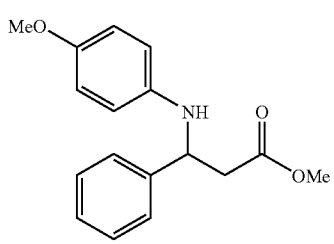

$^1$H NMR (400 MHz, CDCl$_3$): δ 7.39-7.25 (m, 5H, Ar—H), 6.71 (AB, d, J$_{AB}$=8.4 Hz, 2H, Ar—H), 6.56 (AB, d, J$_{AB}$=8.4 Hz, 2H, Ar—H), 4.77 (t, J=6.4 Hz, 1H, CH), 4.32 (br s, 1H, NH), 3.71 (s, 3H, CH$_3$), 3.66 (s, 3H, CH$_3$), 2.84 (d, J=6.4 Hz, 2H, CH$_2$). $^{13}$C NMR (100 MHz, CDCl$_3$): δ 171.7 (Cq, CO), 152.6, 142.0, 140.3 (Cq), 128.8, 127.5, 126.4 (C—Ar), 115.6, 114.7 (C—Ar), 56.2, 55.7 (OCH$_3$), 51.9 (CH), 42.5 (CH$_2$).

Methyl 3-(4-methoxyphenylamino)-3-(4-nitrophenyl)propanoate

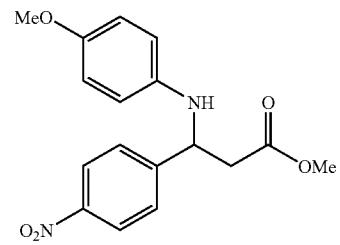

$^1$H NMR (400 MHz, CDCl$_3$): δ 8.18 (AB, d, J$_{AB}$=8.6 Hz, 2H, Ar—H), 7.57 (AB, d, J$_{AB}$=8.6 Hz, 2H, Ar—H), 6.70 (AB, d, J$_{AB}$=8.8 Hz, 2H, Ar—H), 6.48 (AB, d, J$_{AB}$=8.8 Hz, 2H, Ar—H), 4.87 (dd, J=4.6, 6.8 Hz, 1H, CH), 4.30 (br s, 1H, NH), 3.70 (s, 3H, CH$_3$), 3.67 (s, 3H, CH$_3$), 2.83 (dd, J=7.9, 15.3 Hz, 2H, CH$_2$). $^{13}$C NMR (100 MHz, CDCl$_3$): δ 171.1 (Cq, CO), 152.7, 150.2, 147.3, 140.1 (Cq), 127.4, 124.1 (C—Ar), 115.2, 114.8 (C—Ar), 55.6, 55.3 (OCH$_3$), 52.1 (CH), 42.1 (CH$_2$). MS (ESI): m/z 330 (M$^+$), 257, 211, 122, 108.

Methyl 3-(4-methoxyphenylamino)-3-(2-nitrophenyl)propanoate

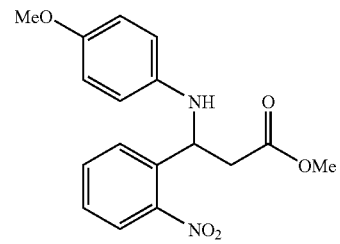

$^1$H NMR (400 MHz, CDCl$_3$): δ 7.97 (dd, J=1.2, 8.0 Hz, 1H, Ar—H), 7.73 (dd, J=1.2, 8.0 Hz, 1H, Ar—H), 7.56 (dt, J=1.2, 8.0 Hz, 1H, Ar—H), 7.41 (dt, J=1.2, 8.0 Hz, 1H, Ar—H), 6.68 (AB, d, J$_{AB}$=8.8 Hz, 2H, Ar—H), 6.45 (AB, d, J$_{AB}$=8.8 Hz, 2H, Ar—H), 5.40 (dd, J=4.3, 7.9 Hz, 1H, CH), 4.30 (br s, 1H, NH), 3.69 (s, 3H, OCH$_3$), 3.67 (s, 3H, OCH$_3$), 3.04 (dd, J=4.3, 15.3 Hz, 1H, CH$_2$), 2.81 (dd, J=7.9, 15.3 Hz, 1H, CH$_2$). $^{13}$C NMR (100 MHz, CDCl$_3$): δ 171.4 (Cq, CO), 152.6, 148.9, 140.0, 137.7 (Cq), 133.6, 128.6, 128.4, 125.0 (C—Ar), 116.4, 114.8 (C—Ar), 55.6, 52.0 (OCH$_3$), 51.4 (CH), 41.2 (CH$_2$). MS (ESI): m/z 330 (e), 296, 257, 237, 122, 108.

Methyl 3-(2-methoxyphenylamino)-3-(2-nitrophenyl)propanoate

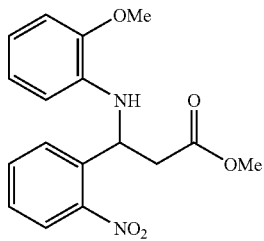

$^1$H NMR (400 MHz, CDCl$_3$): δ 7.98 (dd, J=1.1, 8.0 Hz, 1H, Ar—H), 7.69 (dd, J=1.1, 8.0 Hz, 1H, Ar—H), 7.54 (dt, J=1.1, 8.0 Hz, 1H, Ar—H), 7.40 (dt, J=1.1, 8.0 Hz, 1H, Ar—H), 6.77 (dd, J=1.9, 7.6 Hz, 1H, Ar—H), 6.67 (dq, J=2.0, 7.6 Hz, 2H, Ar—H), 6.25 (dd, J=1.9, 7.6 Hz, 1H, Ar—H), 5.53 (br dd, J=4.3, 7.9 Hz, 1H, CH), 5.39 (br d, J=6.4 Hz, 1H, NH), 3.90 (s, 3H, OCH$_3$), 3.69 (s, 3H, OCH$_3$), 3.08 (dd, J=4.3, 15.3 Hz, 1H, CH$_2$), 2.86 (dd, J=7.9, 15.3 Hz, 1H, CH$_2$). $^{13}$C NMR (100 MHz, CDCl$_3$): δ 171.1 (Cq, CO), 148.8, 146.9, 137.8, 135.7 (Cq), 133.7, 128.4, 128.3, 125.0, 121.1, 117.5, 110.8, 109.6 (C—Ar), 55.6, 52.0 (OCH$_3$), 50.3 (CH), 41.5 (CH$_2$). MS (ESI): m/z 330 (M$^{30}$), 257, 207, 123, 108.

4-(2-Methoxycarbonyl)-1-(4-methoxyphenylamino) ethyl-2-methoxyphenyl trifluoromethane sulfonate

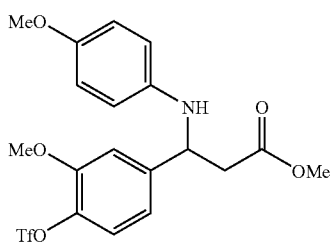

$^1$H NMR (400 MHz, CDCl$_3$): δ 7.18 (d, J=8.4 Hz, 1H, Ar—H), 7.09 (d, J=2.0 Hz, 1H, Ar—H), 6.99 (dd, J=2.0, 8.4 Hz, 1H, Ar—H), 6.73 (AB, d, J$_{AB}$=8.8 Hz, 2H, Ar—H), 6.51 (AB, d, J$_{AB}$=8.8 Hz, 2H, Ar—H), 4.73 (dd, J=5.8, 7.6 Hz, 1H, CH), 4.32 (br s, 1H, NH), 3.89 (s, 3H, CH$_3$), 3.72 (s, 3H, CH$_3$), 3.68 (s, 3H, CH$_3$), 2.79 (ddd, J=5.6, 5.8, 7.6 Hz, 2H, CH$_2$). $^{13}$C NMR (100 MHz, CDCl$_3$): δ 171.4 (Cq, CO), 152.6, 151.6 (Cq), 144.4, 140.5, 137.7 (C—Ar), 117.3 (q, J$_{CF}$=270.4 Hz, Cq, CF$_3$), 122.6, 117.1, 115.2, 114.8 (C—Ar), 111.0 (Cq), 56.2, 55.6 (OCH$_3$), 52.0 (CH), 42.5 (CH$_2$). MS (ESI): m/z 463 (M$^+$), 390, 299, 256, 122.

Methyl 4-(2-methoxycarbonyl)-1-(4-methoxyphenylamino)ethyl)benzoate

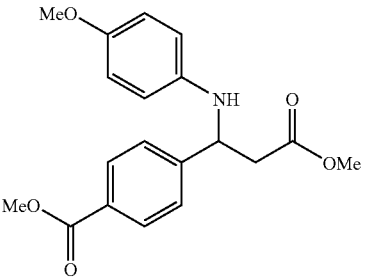

$^1$H NMR (400 MHz, CDCl$_3$): δ 8.00 (AB, J$_{AB}$=8.2 Hz, 2H, Ar—H), 7.45 (AB, J$_{AB}$=8.2 Hz, 2H, Ar—H), 6.69 (AB, d, J$_{AB}$=8.4 Hz, 2H, Ar—H), 6.50 (AB, d, J$_{AB}$=8.4 Hz, 2H, Ar—H), 4.81 (t, J=6.7 Hz, 1H, CH), 4.25 (br s, 1H, NH), 3.90 (s, 3H, CH$_3$), 3.69 (s, 3H, CH$_3$), 3.65 (s, 3H, CH$_3$), 2.80 (dd, J=5.7, 7.6 Hz, 2H, CH$_2$). $^{13}$C NMR (100 MHz, CDCl$_3$): δ 171.4, 166.8 (Cq, CO), 152.5, 147.8, 140.5, 130.1, 129.4 (Cq), 126.4, 115.2, 114.8 (C—Ar), 55.7, 55.6, 52.1 (CH), 52.0 (OCH$_3$), 42.3 (CH$_2$). MS (ESI): m/z 343 (M$^+$), 270, 122, 108.

Methyl 6-(2-methoxycarbonyl)-1-(4-methoxyphenylamino)ethyl)naphthalene-2-carboxylate

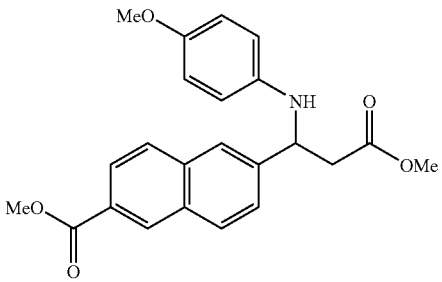

$^1$H NMR (400 MHz, CDCl$_3$): δ 8.58 (s, 1H, Ar—H), 8.05 (dd, J=1.7, 8.5 Hz, 1H, Ar—H), 7.93 (d, J=8.5 Hz, 1H, Ar—H), 7.88 (s, 1H, Ar—H), 7.84 (d, J=8.5 Hz, 1H, Ar—H), 7.57 (dd, J=1.7, 8.5 Hz, 1H, Ar—H), 6.69 (AB, d, J$_{AB}$=8.4 Hz, 2H, Ar—H), 6.57 (AB, d, J$_{AB}$=8.4 Hz, 2H, Ar—H), 4.94 (dd, J=5.7, 7.6 Hz, 1H, CH), 4.30 (br s, 1H, NH), 3.98 (s, 3H, CH$_3$), 3.68 (s, 3H, CH$_3$), 3.67 (s, 3H, CH$_3$), 2.84 (dd, J=5.7, 7.6 Hz, 2H, CH$_2$). $^{13}$C NMR (100 MHz, CDCl$_3$): δ 171.5, 167.2 (Cq, CO), 152.4, 142.7, 140.7, 135.6, 132.0 (Cq), 130.8, 130.1, 128.2 (C—Ar), 127.3 (Cq), 125.6, 125.2, 125.0 (C—Ar), 115.2, 114.8 (C—Ar), 56.0, 55.7, 52.0 (OCH$_3$), 52.3 (CH), 42.5 (CH$_2$).

Methyl 3-(4-methoxyphenylamino)-3-(4-trifluoromethyl)phenyl)propanoate

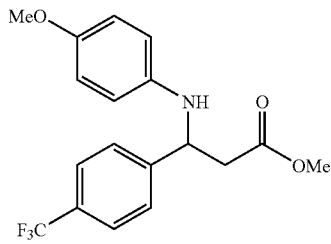

$^1$H NMR (400 MHz, CDCl$_3$): δ 7.59 (AB, J$_{AB}$=8.4 Hz, 2H, Ar—H), 7.51 (AB, J$_{AB}$=8.4 Hz, 2H, Ar—H), 6.72 (AB, d, J$_{AB}$=8.4 Hz, 2H, Ar—H), 6.51 (AB, d, J$_{AB}$=8.4 Hz, 2H, Ar—H), 4.81 (t, J=6.7 Hz, 1H, CH), 4.20 (br s, 1H, NH), 3.71 (s, 3H, CH$_3$), 3.68 (s, 3H, CH$_3$), 2.82 (dd, J=5.6, 7.2 Hz, 2H, CH$_2$). $^{13}$C NMR (100 MHz, CDCl$_3$): δ 171.3 (Cq, CO), 152.6, 146.6, 140.4 (Cq), 129.7 (q, J=32.0 Hz, Cq,), 126.7 (C—Ar), 125.8 (q, J=3.8 Hz, C—Ar), 125.6 (q, J$_{CF}$=270.4 Hz, Cq, CF$_3$), 115.2, 114.8 (C—Ar), 55.6, 55.5 (OCH$_3$), 52.0 (CH), 42.4 (CH$_2$). MS (ESI): m/z 353 (M$^+$), 280, 122, 108.

1-Ethyl 4-methyl
2-(4-methoxyphenylamino)succinate

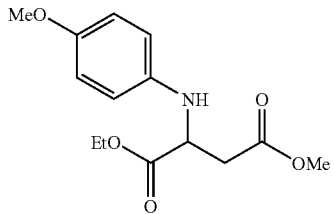

$^1$H NMR (400 MHz, CDCl$_3$): δ 6.78 (AB, d, J$_{AB}$=8.9 Hz, 2H, Ar—H), 6.67 (AB, d, J$_{AB}$=8.9 Hz, 2H, Ar—H), 4.36 (t, J=6.0 Hz, 1H, CH), 4.20 (dq, J=2.5, 7.1 Hz, 2H, CH$_2$), 3.75 (s, 3H, CH$_3$), 3.71 (s, 3H, CH$_3$), 2.85 (d, J=6.0 Hz, 2H, CH$_2$), 2.0 (br s, 1H, NH), 1.85 (t, J=7.1 Hz, 3H, CH$_3$). $^{13}$C NMR (100 MHz, CDCl$_3$): δ 172.5, 171.1 (Cq, CO), 153.2, 140.1 (Cq), 115.9, 114.8 (C—Ar), 61.6 (OCH$_2$), 55.7, 54.9 (OCH$_3$), 52.0 (CH), 37.4 (CH$_2$), 14.1 (CH$_3$). MS (ESI): m/z 281 (M$^+$), 208, 148, 134.

A variety of aryl- and alkyl-substituted α,β-unsaturated aldehydes were observed to form the corresponding isoxazolidin-5-one derivatives and β-amino acid ester derivatives. In general, it was observed that aryl- and alkyl-substituted α,β-unsaturated aldehydes with an electron-withdrawing group provided higher yields. It is worth noting that substrates with different functional groups, including ether, ester, nitro, and sulfonate groups, can be used. (Table 2)

Traces of N-p-hydroxyphenyl β-amino acid ester were observed in some cases.

TABLE 2

NHC-catalyzed Synthesis of N-Phenylisoxazolidin-5-one Derivatives and Corresponding β-Amino Acid Esters

| entry | aldehyde | isoxazolidin-5-one (yield, %$^a$) | β-aminoester | yield, %$^b$ |
|---|---|---|---|---|
| 1 | cinnamaldehyde | (82) | | 75 |
| 2 | 4-nitrocinnamaldehyde | (98) | | 92$^c$ |

TABLE 2-continued

NHC-catalyzed Synthesis of N-Phenylisoxazolidin-5-one Derivatives and Corresponding β-Amino Acid Esters

| entry | aldehyde | isoxazolidin-5-one (yield, %ᵃ) | β-aminoester | yield, %ᵇ |
|---|---|---|---|---|
| 3 | 2-NO₂-cinnamaldehyde | 3-(2-nitrophenyl)-2-phenylisoxazolidin-5-one (84) | methyl 3-(4-methoxyphenylamino)-3-(2-nitrophenyl)propanoate | 75 |
| | | | methyl 3-(2-methoxyphenylamino)-3-(2-nitrophenyl)propanoate | 5 |
| 4 | 3-MeO-4-TfO-cinnamaldehyde | 3-(3-methoxy-4-triflyloxyphenyl)-2-phenylisoxazolidin-5-one (81) | methyl 3-(4-methoxyphenylamino)-3-(3-methoxy-4-triflyloxyphenyl)propanoate | 78 |
| 5 | 4-MeOOC-cinnamaldehyde | 3-(4-methoxycarbonylphenyl)-2-phenylisoxazolidin-5-one (88) | methyl 3-(4-methoxyphenylamino)-3-(4-methoxycarbonylphenyl)propanoate | 85 |

TABLE 2-continued

NHC-catalyzed Synthesis of N-Phenylisoxazolidin-5-one Derivatives and Corresponding β-Amino Acid Esters

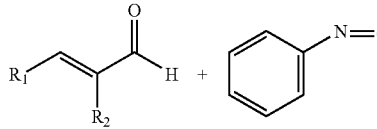

| entry | aldehyde | isoxazolidin-5-one (yield, %<sup>a</sup>) | β-aminoester | yield, %<sup>b</sup> |
|---|---|---|---|---|
| 6 | 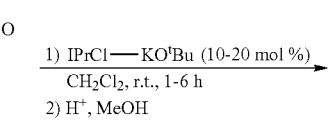 | 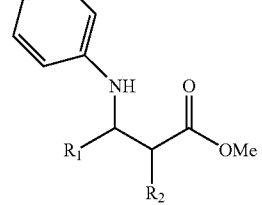 (84) | 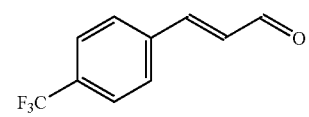 | 80 |
| 7 | 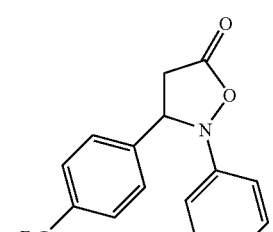 | 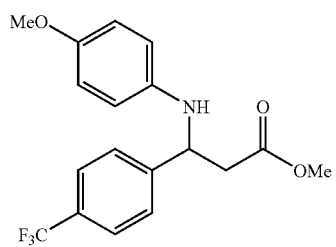 (90) | 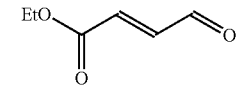 | 88 |
| 8 | 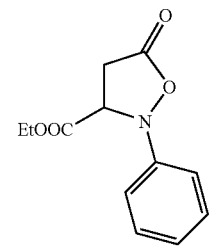 | 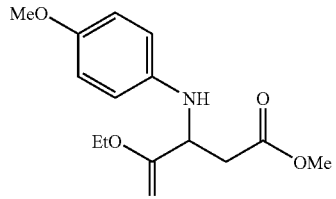 (96) | | 91 |

<sup>a</sup>Yield determined by <sup>1</sup>H NMR and GC-MS analyses.
<sup>b</sup>Isolated yield of the β-amino acid ester with respect to the aldehyde.
<sup>c</sup>10 mol % catalyst was used.

Experiments were also conducted by reacting the following α,β-unsaturated aldehydes represented by the formula (II) as defined above, all with nitrosobenzene in the presence of the IPrCl catalyst (10-20 mol %), KO<sup>t</sup>Bu and CH$_2$Cl$_2$ (r.t., 1-6 h) forming the corresponding N-phenylisoxazolidin-5-one derivatives in the following yields a (%, determined by $^1$H NMR), and then treating the N-phenylisoxazolidin-5-one derivatives with MeOH in the presence of an acid catalyst (r.t., 12 h) forming the corresponding β-amino acid ester derivatives in the following yields b (%):

i) R$_1$=3-Br-4-OTfPh and R$_2$=H; yield a=83%; yield b=79%.
ii) R$_1$=4-CNPh and R$_2$=H; yield a=95%; yield b=40%.
iii) R$_1$=C$_6$F$_5$ and R$_2$=H; yield a=85%; yield b=72%.
iv) R$_1$=3,5-F$_2$Ph and R$_2$=H; yield a=88%; yield b=78%.
v) R$_1$=C$_4$H$_9$ and R$_2$=H; yield a=40%; yield b=30%.

Enantiomeric selectivity was observed in one study using a NHC catalyst derived from a chiral imidazolium salt, which is represented by way of example, and without limitation, by the following scheme:

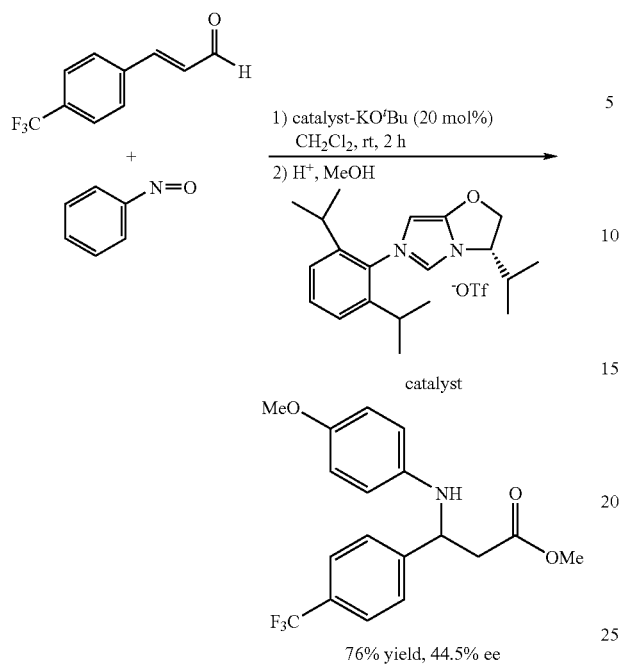

The reaction of the homoenolate with nitrosobenzene may be directed to 1,4- or 1,2-addition by modifying steric and/or electronic properties of the NHC catalyst according to routine experiments.

The present invention includes isomers such as geometrical isomers, optical isomers based on asymmetric carbon, stereoisomers and tautomers and is not limited by the description of the formula illustrated for the sake of convenience.

Although the foregoing invention has been described in some detail by way of illustration and example, and with regard to one or more embodiments, for the purposes of clarity of understanding, it is readily apparent to those of ordinary skill in the art in light of the teachings of this invention that certain changes, variations and modifications may be made thereto without departing from the spirit or scope of the invention as described in the appended claims.

It must be noted that as used in the specification and the appended claims, the singular forms of "a", "an" and "the" include plural reference unless the context clearly indicates otherwise.

Unless defined otherwise all technical and scientific terms used herein have the same meaning as commonly understood to one of ordinary skill in the art to which this invention belongs.

All publications, patents and patent applications cited in this specification are incorporated herein by reference as if each individual publication, patent or patent application were specifically and individually indicated to be incorporated by reference. The citation of any publication, patent or patent application in this specification is not an admission that the publication, patent or patent application is prior art.

The invention claimed is:

1. A process for preparing a N-phenylisoxazolidin-5-one derivative comprising reacting an α,β-unsaturated aldehyde with nitrosobenzene in the presence of a N-heterocyclic carbene (NHC) catalyst.

2. The process according to claim 1 for preparing a N-phenylisoxazolidin-5-one derivative represented by the formula (I):

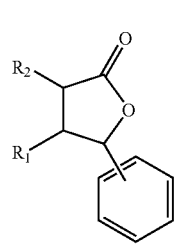

wherein:
$R_1$ is a hydrogen atom, a halogen atom, a nitrile group, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different, a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{2-6}$ alkynyl group which may be substituted with one or more substituents which are the same or different, a 4- to 10-membered non-aromatic heterocyclic group containing one or more heteroatoms which are independently nitrogen, sulfur or oxygen and which group may be substituted with one or more substituents which are the same or different, a 5- to 14-membered aromatic heterocyclic group containing one or more heteroatoms which are independently nitrogen, sulfur or oxygen and which group may be substituted with one or more substituents which are the same or different or a $C_{1-6}$ alkoxycarbonyl group which may be substituted with one or more substituents which are the same or different; and $R_2$ is a hydrogen atom, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different or a $C_{3-8}$ cycloalkenyl group which may be substituted with one or more substituents which are the same or different, which process comprises reacting an α,β-unsaturated aldehyde represented by the formula (II):

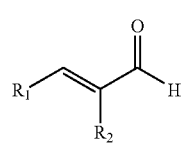

wherein each of $R_1$ and $R_2$ is as defined above, with nitrosobenzene in the presence of a NHC catalyst.

3. The process according to claim 2, wherein in the formulae (I) and (II), each of the $C_{1-6}$ alkyl, $C_{2-6}$ alkenyl, $C_{2-6}$ alkynyl, $C_{3-8}$ cycloalkyl, $C_{3-8}$ cycloalkenyl, $C_{6-14}$ aryl, $C_{6-14}$ aryl-$C_{1-6}$ alkyl, $C_{6-14}$ aryl-$C_{2-6}$ alkenyl, $C_{6-14}$ aryl-$C_{2-6}$ alkynyl, 4- to 10-membered non-aromatic heterocyclic, 5- to 14-membered aromatic heterocyclic and $C_{1-6}$ alkoxycarbonyl groups may be substituted with 1 to 3 substituents which are independently a halogen atom, a hydroxyl group, a thiol group, a nitro group, a nitrile group, a cyano group, a $C_{1-6}$ alkyl, $C_{2-6}$ alkenyl or $C_{2-6}$ alkynyl group which may be substituted with a halogen atom, a $C_{3-8}$ cycloalkyl or $C_{3-8}$cycloalkenyl group which may be substituted, a $C_{6-14}$ aryl group which may be substituted, a 4- to 10-membered non-aromatic heterocylic group containing 1 to 4 heteroatoms which are independently nitrogen, oxygen or sulfur and which group may be substituted, a 5- to 14-membered aromatic heterocylic group containing 1 to 4 heteroatoms which are independently nitrogen, oxygen or sulfur and which group may be substituted, a $C_{1-6}$ alkoxy group which may be substituted, a $C_{3-8}$ cycloalkoxy group which may be substituted, a $C_{1-6}$ alkylthio, $C_{2-6}$ alkenylthio or $C_{2-6}$ alkynylthio group which may be substituted, a $C_{3-8}$ cycloalkylthio or $C_{3-8}$ cycloalkenylthio group which may be substituted, a $C_{6-14}$ aryloxy group which may be substituted, a 4- to 10-membered non-aromatic heterocycle-oxy group which may be substituted, a 5- to 14-membered aromatic heterocycle-oxy group which may be substituted, a $C_{6-14}$ arylthio group which may be substituted, a 4- to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a $C_{1-6}$ imidoyl group, a carbonyl group which is substituted, a carbonyl-oxy group which is substituted, a carboxy group, a carbamoyl group which may be substituted, a $C_{1-4}$ alkylenedioxy group, a sulfinyl group which is substituted, a sulfonyl which is substituted with a trifluoromethyl group, a $C_{1-6}$ alkoxycarbonyl group, a $C_{1-6}$ alkylsulfonyl group, an oxo group or a $C_{1-6}$ alkoxyimino group.

4. The process according to claim 2, wherein in the formulae (I) and (II), $R_1$ is a $C_{1-6}$ alkoxycarbonyl group or a $C_{6-14}$ aryl group which may be substituted with 1 to 3 substituents which are independently nitro, trifluoromethyl, trifluoromethylsulfonyl, methoxy or methoxycarbonyl; and $R_2$ is a hydrogen atom.

5. The process according to claim 1 for preparing a N-phenylisoxalidin-5-one derivative represented by the formula:

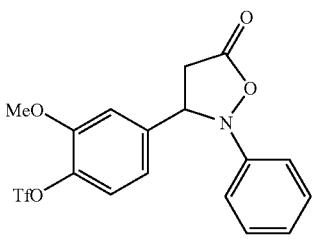

comprising reacting an α,β-unsaturated aldehyde represented by the formula:

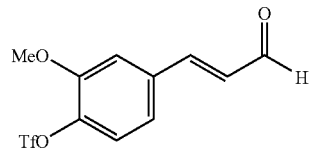

with nitrosobenzene in the presence of a NHC catalyst.

6. A process for preparing an N-alkoxyphenyl protected n-amino acid ester derivative comprising reacting an α,β-unsaturated aldehyde with nitrosobenzene in the presence of a N-heterocyclic carbene (NHC) catalyst to form a N-phenyl-isoxazolidin-5-one derivative and then treating the N-phenyl-isoxazolidin-5-one derivative with an alcohol in the presence of an acid catalyst.

7. The process according to claim 6 for preparing an N-alkoxyphenyl protected β-amino acid ester derivative represented by the formula (IV):

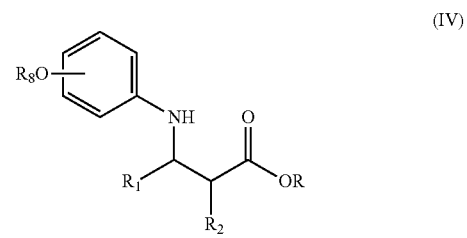

wherein:
$R_1$ is a hydrogen atom, a halogen atom, a nitrile group, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different, a $C_{3-8}$ cycloalkenyl group which may be substituted with one or more substituents which are the same or different, a $C_{6-14}$ aryl group which may be substituted with one or more substituents which are the same or different, alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{2-6}$ alkynyl group which may be substituted with one or more substituents which are the same or different, a 4- to 10-membered non-aromatic heterocyclic group containing one or more heteroatoms which are independently nitrogen, sulfur or oxygen and which group may be substituted with one or more substituents which are the same or different, a 5- to 14-membered aromatic heterocyclic group containing one or more heteroatoms which are independently nitrogen, sulfur or oxygen and which group may be substituted with one or more substituents which are the same or different or a $C_{1-6}$ alkoxycarbonyl group which may be substituted with one or more substituents which are the same or different;
$R_2$ is a hydrogen atom, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different or a $C_{3-8}$ cycloalkenyl group which may be substituted with one or more substituents which are the same or different; and $R_8$ is a $C_{1-6}$ alkyl group, which process comprises:

(a) reacting an α,β-unsaturated aldehyde represented by the formula (II):

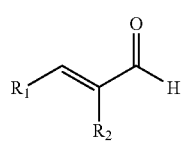

wherein each of $R_1$ and $R_2$ is as defined above, with nitrosobenzene in the presence of a NHC catalyst to form a N-phenylisoxazolidin-5-one derivative represented by the formula (I):

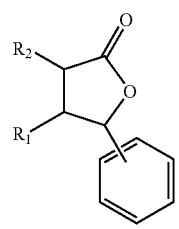

wherein each of $R_1$ and $R_2$ is as defined above; and (b) then treating the N-phenylisoxazolidin-5-one derivative with an alcohol represented by the formula $R_8OH$ wherein $R_8$ is as defined above, in the presence of an acid catalyst.

8. The process according to claim 7, wherein for each of $R_1$ and $R_2$ in the formulae (I), (II) and (IV), each of the $C_{1-6}$ alkyl, $C_{2-6}$ alkenyl, $C_{2-6}$ alkynyl, $C_{3-8}$ cycloalkyl, $C_{3-8}$ cycloalkenyl, $C_{6-14}$ aryl, $C_{6-14}$ aryl-$C_{1-6}$ alkyl, $C_{6-14}$ aryl-$C_{2-6}$ alkenyl, $C_{6-14}$ aryl-$C_{2-6}$ alkynyl, 4- to 10-membered non-aromatic heterocyclic, 5- to 14-membered aromatic heterocyclic and $C_{1-6}$ alkoxycarbonyl groups may be substituted with 1 to 3 substituents which are independently a halogen atom, a hydroxyl group, a thiol group, a nitro group, a nitrile group, a cyano group, a $C_{1-6}$ alkyl, $C_{2-6}$ alkenyl or $C_{2-6}$ alkynyl group which may be substituted with a halogen atom, a $C_{3-8}$ cycloalkyl or $C_{3-8}$ cycloalkenyl group which may be substituted, a $C_{6-14}$ aryl group which may be substituted, a 4- to 10-membered non-aromatic heterocylic group containing 1 to 4 heteroatoms which are independently nitrogen, oxygen or sulfur and which group may be substituted, a 5- to 14-membered aromatic heterocyclic group containing 1 to 4 heteroatoms which are independently nitrogen, oxygen or sulfur and which group may be substituted, a $C_{1-6}$ alkoxy group which may be substituted, a $C_{3-8}$ cycloalkoxy group which may be substituted, a $C_{1-6}$ alkylthio, $C_{2-6}$ alkenylthio or $C_{2-6}$ alkynylthio group which may be substituted, a $C_{3-8}$ cycloalkylthio or $C_{3-8}$ cycloalkenylthio group which may be substituted, a $C_{6-14}$ aryloxy group which may be substituted, a 4- to 10-membered non-aromatic heterocycle-oxy group which may be substituted, a 5- to 14-membered aromatic heterocycle-oxy group which may be substituted, a $C_{6-14}$ arylthio group which may be substituted, a 4- to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a $C_{1-6}$ imidoyl group, a carbonyl group which is substituted, a carbonyl-oxy group which is substituted, a carboxy group, a carbamoyl group which may be substituted, a $C_{1-4}$ alkylenedioxy group, a sulfinyl group which is substituted, a sulfonyl which is substituted with a trifluoromethyl group, a $C_{1-6}$ alkoxycarbonyl group, a $C_{1-6}$ alkylsulfonyl group, an oxo group or a $C_{1-6}$ alkoxyimino group.

9. The process according to 7, wherein in the formulae (I), (II), (IV) and $R_8OH$, $R_1$ is a $C_{1-6}$ alkoxycarbonyl group or a $C_{6-14}$ aryl group which may be substituted with 1 to 3 substituents which are independently nitro, trifluoromethyl, trifluoromethylsulfonyl, methoxy or methoxycarbonyl; $R_2$ is hydrogen atom; and $R_3$ is methyl.

10. The process according to claim 6 for preparing an N-alkoxyphenyl protected β-amino acid ester derivative represented by the formula:

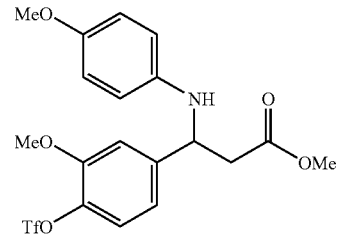

comprising reacting an α,β-unsaturated aldehyde represented by the formula:

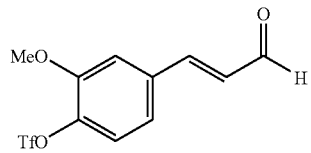

with nitrosobenzene in the presence of a NHC catalyst to form a N-phenylisoxalidin-5-one derivative represented by the formula:

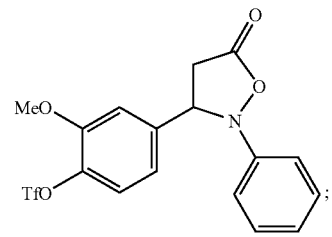

and
then treating the N-phenylisoxalidin-5-one derivative with methanol in the presence of an acid catalyst.

11. The process according to 1, wherein the NHC catalyst is derived from an imidazolium salt.

12. The process according to claim 11, wherein the imidazolium salt is represented by the formula (V):

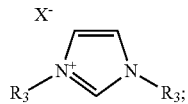

the formula (VI):

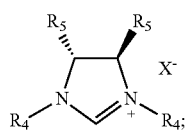

the formula (VII):

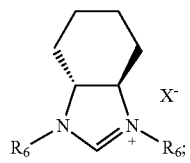

the formula

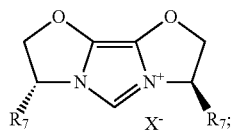

the formula:

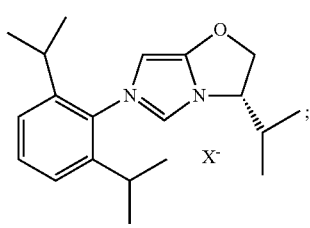

the formula:

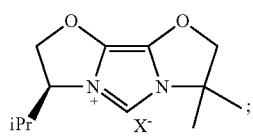

the formula:

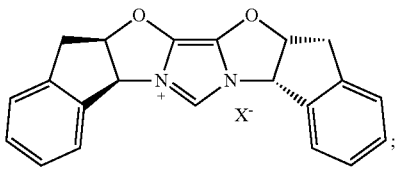

the formula:

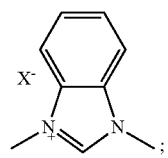

the formula

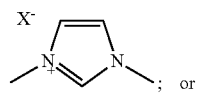; or the formula:

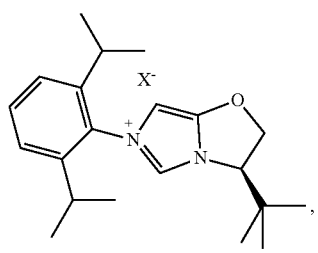

wherein $R_3$ is Ph, $^i$Pr, Mes or 2,6-$^i$Pr-Ph; $R_4$ is 2,6-$^i$Pr-Ph; $R_5$ is hydrogen or Ph; $R_6$ is 2,6-$^i$Pr-Ph; $R_7$ is $^i$Pr or t-Bu; and $X^-$ is $Br^-$, $BF_4^-$, $Cl^-$ or $^-OTf$.

13. A process for preparing an N-alkoxyphenyl protected β-amino acid ester derivative comprising treating a N-phenylisoxazolidin-5-one derivative with an alcohol in the presence of an acid catalyst.

14. The process according to claim 13 for preparing an N-alkoxyphenyl protected β-amino acid ester derivative represented by the formula (IV):

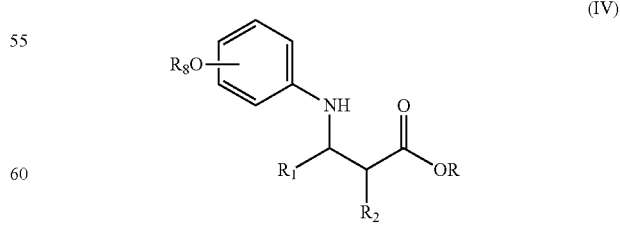

wherein:
$R_1$ is a hydrogen atom, a halogen atom, a nitrile group, a $C_{1-6}$ alkyl group which ma be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{1-6}$ alkenyl group which may be substituted with one or more substituents which are the same or different, a 4- to 10-membered non-aromatic heterocyclic group containing one or more heteroatoms which are independently nitrogen, sulfur or oxygen and which group may be substituted with one or more substituents which are the same or different, a 5- to 14-membered aromatic heterocyclic group containing one or more heteroatoms which are independently nitrogen, sulfur or oxygen and which group may be substituted with one or more substituents which are the same or different or a $C_{1-6}$ alkoxycarbonyl group which may be substituted with one or more substituents which are the same or different;

$R_2$ is a hydrogen atom, a $C_{1-6}$ alkyl group which may be substituted with one or more substituents which are the same or different, a $C_{2-6}$ alkenyl group which may be substituted with one or more substituents which are the same or different a $C_{2-6}$ which may be substituted with one or more substituents which are the same or different, a $C_{3-8}$ cycloalkyl group which may be substituted with one or more substituents which are the same or different or a $C_{3-8}$ cycloalkenyl group which may be substituted with one or more substituents which are the same or different; and $R_8$ is a $C_{1-6}$ alkyl group, which process comprises treating a N-phenylisoxazolidin-5-one derivative represented by the formula (I):

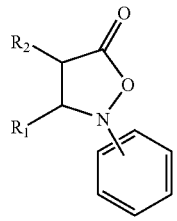

(I)

wherein each of $R_1$ and $R_2$ is as defined above, with an alcohol represented by the formula $R_8OH$ wherein $R_8$ is as defined above, in the presence of an acid catalyst.

15. The process according to claim 14, wherein for each of $R_1$ and $R_2$ in the formulae (I) and (N), each of the $C_{1-6}$ alkyl, $C_{2-6}$ alkenyl, $C_{2-6}$ alkynyl, $C_{3-8}$ cycloalkyl, $C_{3-8}$ cycloalkenyl, $C_{6-14}$ aryl, $C_{6-14}$ aryl-$C_{1-6}$ alkyl, $C_{6-14}$ aryl-$C_{2-6}$ alkenyl, $C_{6-14}$ aryl-$C_{2-6}$ alkynyl, 4- to 10-membered non-aromatic heterocyclic, 5- to 14-membered aromatic heterocyclic and $C_{1-6}$ alkoxycarbonyl groups may be substituted with 1 to 3 substituents which are independently a halogen atom, a hydroxyl group, a thiol group, a nitro group, a nitrile group, a cyano group, a $C_{1-6}$ alkyl, $C_{2-6}$ alkenyl or $C_{2-6}$ alkynyl group which may be substituted with a halogen atom, a $C_{3-4}$ cycloalkyl or $C_{3-4}$ cycloalkenyl group which may be substituted, a $C_{6-14}$ aryl group which may be substituted, a 4- to 10-membered non-aromatic heterocylic group containing 1 to 4 heteroatoms which are independently nitrogen, oxygen or sulfur and which group may be substituted, a 5- to 14-membered aromatic heterocylic group containing 1 to 4 heteroatoms which are independently nitrogen, oxygen or sulfur and which group may be substituted, a $C_{1-6}$ alkoxy group which may be substituted, a $C_{3-4}$ cycloalkoxy group which may be substituted, a $C_{1-6}$ alkylthio, $C_{2-6}$ alkenylthio or $C_{2-6}$ alkynylthio group which may be substituted, a $C_{3-8}$ cycloalkylthio or $C_{3-8}$ cycloalkenylthio group which may be substituted, a $C_{6-14}$ aryloxy group which may be substituted, a 4- to 10-membered non-aromatic heterocycle-oxy group which may be substituted, a 5- to 14-membered aromatic heterocycle-oxy group which may be substituted, a $C_{6-14}$ arylthio group which may be substituted, a 4- to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a $C_{1-6}$ imidoyl group, a carbonyl group which is substituted, a carbonyl-oxy group which is substituted, a carboxy group, a carbamoyl group which may be substituted, a $C_{1-4}$ alkylenedioxy group, a sulfinyl group which is substituted, a sulfonyl which is substituted with a trifluoromethyl group, a $C_{1-6}$ alkoxycarbonyl group, a $C_{1-6}$ alkylsulfonyl group, an oxo group or a $C_{1-6}$ alkoxyimino group.

16. The process according to claim 14, wherein in the formulae (I), (IV) and $R_8OH$, $R_1$ is a $C_{1-6}$ alkoxycarbonyl group or a $C_{6-14}$ aryl group which may be substituted with 1 to 3 substituents which are independently nitro, trifluoromethyl, trifluoromethylsulfonyl, methoxy or methoxycarbonyl; $R_2$ is a hydrogen atom; and $R_8$ is methyl.

17. The process according to claim 13 for preparing an N-alkoxyphenyl protected β-amino acid ester derivative represented by the formula:

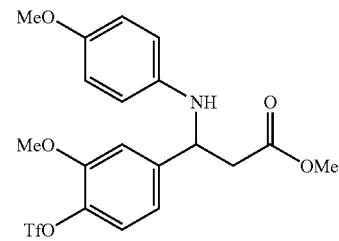

comprising treating a N-phenylisoxalidin-5-one derivative represented by the formula:

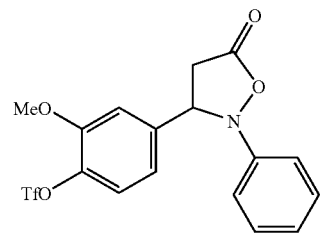

with methanol in the presence of an acid catalyst.

18. The process according to claim 6, wherein the NHC catalyst is derived from an imidazolium salt.

19. The process according to claim 18, wherein the imidazolium salt is represented by:

the formula (V):

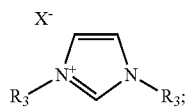 (V)

the formula (VI):

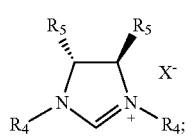 (VI)

the formula (VII):

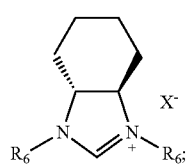 (VII)

the formula:

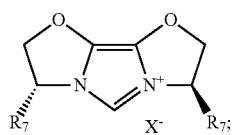

the formula

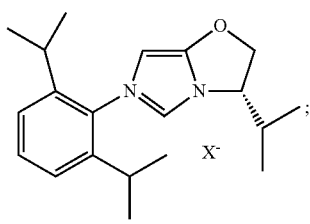

the formula:

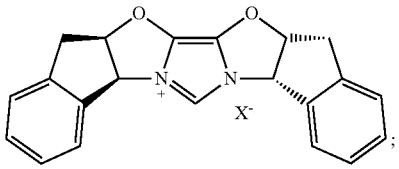

the formula:

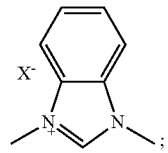

the formula:

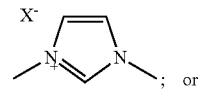

the formula:

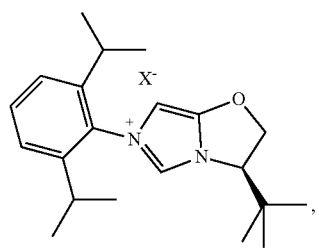; or the formula:

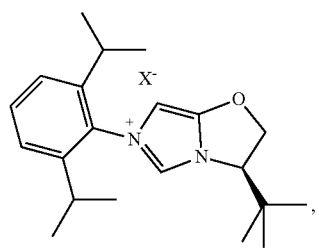, wherein $R_3$ is $^iPh$, $^iPr$, Mes or 2,6-$^iPr$-Ph; $R_4$ is 2,6-$^iPr$-Ph; $R_5$ is hydrogen or Ph; $R_6$ is 2,6-$^iPr$-Ph; $R_7$ is $^iPr$ or t-Bu; and $X^-$ is $Br^-$, $BF_4^-$, $Cl^-$ or $^-OTf$.

* * * * *

UNITED STATES PATENT AND TRADEMARK OFFICE
CERTIFICATE OF CORRECTION

PATENT NO. : 8,071,783 B2
APPLICATION NO. : 12/531678
DATED : December 6, 2011
INVENTOR(S) : Yugen Zhang and Jackie Y. Ying et al.

It is certified that error appears in the above-identified patent and that said Letters Patent is hereby corrected as shown below:

Column 37
Claim 3, line 14, replace "... or $C_{3-8}$cy-" with -- ...or $C_{3-8}$ cy- --

Column 38
Claim 6, line 11, replace "n-amino acid..." with -- β-amino acid... --

Column 38
Claim 7, line 46, replace "... or different, alkyl" with -- ... or different, a $C_{6-14}$ aryl-$C_{1-6}$ alkyl --

Column 40
Claim 9, line 20, replace "... $R_3$ is methyl." with -- ... $R_8$ is methyl. --

Column 40
Claim 11, line 66, replace "... according to 1, ..." with -- ... according to claim 1, ... --

Column 41
Claim 12, line 35, replace "the formula" with -- the formula: --

Column 42
Claim 12, line 20, replace "the formula" with -- the formula: --

Column 42
Claim 14, line 66, replace "... which ma be ..." with -- ... which may be ... --

Column 43
Claim 14, line 16, replace "... a $C_{6-14}$ aryl-$C_{1-6}$ alkenyl ..." with -- ... a $C_{6-14}$ aryl-$C_{2-6}$ alkenyl ... --

Signed and Sealed this
Eleventh Day of September, 2012

David J. Kappos
*Director of the United States Patent and Trademark Office*

CERTIFICATE OF CORRECTION (continued)
U.S. Pat. No. 8,071,783 B2

Column 43
Claim 14, line 34, replace "same or different a $C_{2-6}$ which ..." with -- same or different, a $C_{2-6}$ alkynyl group which ... --

Column 43
Claim 15, line 60, replace "... in the formulae (I) and (N), ..." with -- ... in the formulae (I) and (IV), ... --

Column 44
Claim 15, line 2, replace "... atom, a $C_{3-4}$ cycloalkyl or" with -- ... atom, a $C_{3-8}$ cycloalkyl or --

Column 44
Claim 15, line 3, replace "$C_{3-4}$ cycloalkenyl group..." with -- $C_{3-8}$ cycloalkenyl group... --

Column 44
Claim 15, line 11, replace "stituted, a $C_{3-4}$ cycloalkoxy group..." with -- stituted, a $C_{3-8}$ cycloalkoxy group... --

Column 45
Claim 19, line 45, replace "the formula" with -- the formula: --

Column 46
Claim 19, line 52, replace "wherein $R_3$ is $^{i}Ph$, ..." with -- wherein $R_3$ is Ph, ... --